United States Patent
Cheng et al.

(10) Patent No.: US 7,186,523 B2
(45) Date of Patent: Mar. 6, 2007

(54) METHOD FOR SYNTHESIS OF ARYL-CAROTENOIDS

(75) Inventors: Qiong Cheng, Wilmington, DE (US); Luan Tao, Claymont, DE (US); Pierre E. Rouvier, Wilmington, DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 608 days.

(21) Appl. No.: 10/430,129

(22) Filed: May 5, 2003

(65) Prior Publication Data

US 2005/0214896 A1 Sep. 29, 2005

Related U.S. Application Data

(60) Provisional application No. 60/378,312, filed on May 6, 2002.

(51) Int. Cl.
| | |
|---|---|
| C12P 23/00 | (2006.01) |
| C07H 21/04 | (2006.01) |
| C12N 9/10 | (2006.01) |
| C12N 1/21 | (2006.01) |
| C12N 15/74 | (2006.01) |

(52) U.S. Cl. ............ 435/67; 435/193; 435/252.3; 435/471; 435/419; 435/468; 536/23.2; 800/282

(58) Field of Classification Search ............ 435/67, 435/193, 468, 252.3, 471, 419; 536/23.2; 800/282
See application file for complete search history.

(56) References Cited

FOREIGN PATENT DOCUMENTS

WO    WO 02/18617 A2    3/2002

OTHER PUBLICATIONS

Lee et al. Biosynthesis of Structurally Novel Carotenoids in *Escherichia coli*. 2003. Chemistry and Biology, vol. 10, 453-462.*
G. Armstrong, Carotenoid Genetics and Biochemistry, 1999, In Comprehensive Natural Products Chemistry, Elsevier Press, vol. 2, pp. 321-352.
Krugel et al., Functional analysis of genes from *Streptomyces griseus* involved in the synthesis of isorenieratene, a carotenoid with aromatic end groups, revealed a novel type of carotenoid desaturase, Biochimica et Biophysica Acta, 1439: pp. 57-64, 1999.
Krubasik and Sandmann, A carotenogenic gene cluster from *Brevibacterium linens* with novel lycopene cyclase genes involved in the synthesis of aromatic carotenoids, Mol. Gen. Genet, 263: pp. 423-432, 2000.
Viveiros et al., Structural and functional analysis of the gene cluster encoding carotenoid biosynthesis in *Mycobacterium aurum* A+, FEMS Microbiol Lett, 187: 95-101, 2000.
Liaaen-Jensen et al., Bacterial Carotenoids, Acta Chem. Scand., 18: 1703-1718, 1964.
Takaichi et al., New carotenoids from the termophilic green sulfur bacterium Chlorobium tepidum: 1', 2'-dihydro-γ—carotene, 1', 2'-dihydrochlorobactene, and OH-chlorobactene glucoside ester, and the carotenoid composition of different strains, Arch Microbiol., 168: pp. 270-276, 1997.
Eisen et al., The complete genome sequence of *Chloroblum tepidum* TLS, a photosynthetic, anaerobic, green-sulfur baterium, PNAS USA, 99: 9509-9514, 2002.
Schumann et al., Activation and analysis of cryptic crt genes fro carotenoid biosynthesis from *Streptomyces griseus*, Mil. Gen Genet, 252: 658-666, 1996.
Kohl et al., The Pigments of *Brevibacterium Linens*: Aromatic Carotenoids, Phytochemistry, 22: pp. 207-213, 1983.
GenBank Accession No. AF139916, Shuttle vector pDA71, Jan. 25, 2001.
GenBank Accession No. AJ308376, *Brevibacterium linens*, Jun. 15, 2000.
White, O. et al., Genome sequence of the radio-resistant bacterium *Deinococcus radiodurans* R1 Science, 286, 5444, pp. 1571-1577, 1999.

* cited by examiner

*Primary Examiner*—Ponnathapura Achutamurthy
*Assistant Examiner*—Kagnew Gebreyesus

(57) ABSTRACT

A method for the production of aryl-carotenoids is provided through bioconversion of cyclic carotenoids having at least one β-ionone ring. Expression of a heterologous gene encoding a carotene desaturase (crtU) enzyme in a host cell that produces a suitable cyclic carotenoid substrate effect the production of aryl carotenoids.

4 Claims, 6 Drawing Sheets

TLC (Silica Gel 60)
7.5% acetone in hexane

SEQUENCE LISTING

```
<160> NUMBER OF SEQ ID NOS: 24

<210> SEQ ID NO 1
<211> LENGTH: 19
<212> TYPE: DNA
<213> ORGANISM: artificial sequence
<220> FEATURE:
<223> OTHER INFORMATION: Primer

<400> SEQUENCE: 1
gagtttgatc ctggctcag                                              19

<210> SEQ ID NO 2
<211> LENGTH: 16
<212> TYPE: DNA
<213> ORGANISM: artificial sequence
<220> FEATURE:
<223> OTHER INFORMATION: Primer

<400> SEQUENCE: 2
taccttgtta cgactt                                                 16

<210> SEQ ID NO 3
<211> LENGTH: 17
<212> TYPE: DNA
<213> ORGANISM: artificial sequence
<220> FEATURE:
<223> OTHER INFORMATION: Primer
<220> FEATURE:
<221> NAME/KEY: misc_feature
<222> LOCATION: (11)..(11)
<223> OTHER INFORMATION: Y = C or T
<220> FEATURE:
<221> NAME/KEY: misc_feature
<222> LOCATION: (12)..(12)
<223> OTHER INFORMATION: M = A or C

<400> SEQUENCE: 3
gtgccagcag ymgcggt                                                17

<210> SEQ ID NO 4
<211> LENGTH: 1424
<212> TYPE: DNA
<213> ORGANISM: Rhodococcus erythropolis AN12

<400> SEQUENCE: 4
tcgagcggta gagagaagct tgcttctctt gagagcggcg gacgggtgag taatgcctag    60
gaatctgcct ggtagtgggg gataacgttc ggaaacggac gctaataccg catacgtcct   120
acgggagaaa gcaggggacc ttcgggcctt gcgctatcag atgagcctag gtcggattag   180
```

```
ctagttggtg aggtaatggc tcaccaaggc gacgatccgt aactggtctg agaggatgat    240
cagtcacact ggaactgaga cacggtccag actcctacgg gaggcagcag tggggaatat    300
tggacaatgg gcgaaagcct gatccagcca tgccgcgtgt gtgaagaagg tcttcggatt    360
gtaaagcact ttaagttggg aggaagggca gttacctaat acgtgattgt tttgacgtta    420
ccgacagaat aagcaccggc taactctgtg ccagcagccg cggtaataca gagggtgcaa    480
gcgttaatcg gaattactgg gcgtaaagcg cgcgtaggtg gtttgttaag ttggatgtga    540
aatccccggg ctcaacctgg gaactgcatt caaaactgac tgactagagt atggtagagg    600
gtggtggaat tcctgtgta gcggtgaaat gcgtagatat aggaaggaac accagtggcg    660
aaggcgacca cctggactga tactgacact gaggtgcgaa agcgtgggga gcaaacagga    720 ttagatacc  tggtagtcca cgccgtaaac gatgtcaact agccgttggg agccttgagc    780
tcttagtggc gcagctaacg cattaagttg accgcctggg gagtacggcc gcaaggttaa    840
aactcaaatg aattgacggg ggcccgcaca agcggtggag catgtggttt aattcgaagc    900
aacgcgaaga accttaccag gccttgacat ccaatgaact ttctagagat agattggtgc    960
cttcgggaac attgagacag gtgctgcatg gctgtcgtca gctcgtgtcg tgagatgttg   1020
ggttaagtcc cgtaacgagc gcaacccttg tccttagtta ccagcacgta atggtgggca   1080
ctctaaggag actgccggtg acaaaccgga ggaaggtggg gatgacgtca agtcatcatg   1140
gcccttacgg cctgggctac acacgtgcta caatggtcgg tacagagggt tgccaagccg   1200
cgaggtggag ctaatcccag aaaaccgatc gtagtccgga tcgcagtctg caactcgact   1260
gcgtgaagtc ggaatcgcta gtaatcgcga atcagaatgt cgcggtgaat acgttcccgg   1320
gccttgtaca caccgcccgt cacaccatgg gagtgggttg caccagaagt agctagtcta   1380
accctcggga ggacggttac cacggtgtga ttcatgactg ggt                     1424
```

<210> SEQ ID NO 5
<211> LENGTH: 27
<212> TYPE: DNA
<213> ORGANISM: artificial sequence
<220> FEATURE:
<223> OTHER INFORMATION: Primer

<400> SEQUENCE: 5

```
ccatggtctg cgcacctcat gatccga                                         27
```

<210> SEQ ID NO 6
<211> LENGTH: 27
<212> TYPE: DNA
<213> ORGANISM: artificial sequence
<220> FEATURE:
<223> OTHER INFORMATION: Primer

<400> SEQUENCE: 6

```
ccatggaatg aagcggtcga ggacgga                                         27
```

<210> SEQ ID NO 7
<211> LENGTH: 1599
<212> TYPE: DNA
<213> ORGANISM: Rhodococcus erythropolis AN12

<400> SEQUENCE: 7

```
gtgagcgcat ttctcgacgc cgtcgtcgtc ggttccggac acaacgcgct cgtttcggcc     60
gcgtatctcg cacgtgaggg ttggtcggtc gaggttctcg agaaggacac ggttctcggc    120
```

```
ggtgccgtct cgaccgtcga gcgatttccc ggatacaagg tggaccgggg gtcgtctgcg      180
cacctcatga tccgacacag tggcatcatc gaggaactcg gactcggcgc gcacggcctt      240
cgctacatcg actgtgaccc gtgggcgttc gctccgcccg ccctggcac cgacgggccg       300 ggcatcgtgt tcatcgcga cctcgatgca acctgccagt ccatcgaacg agcttgcggg       360
acaaaggacg ccgacgcgta ccggcggttc gtcgcggtct ggtcggagcg cagccgacac      420
gtgatgaagg cattttccac accgcccacc ggatcgaacc tgatcggtgc gttcggagga     480
ctggccacag cgcgcggcaa cagcgaactg tcgcggcagt tcctcgcgcc gggcgacgca      540
ctgctggacg agtatttcga cagtgaggca ctcaaggcag cgttggcgtg gttcggcgcc     600
cagtccgggc ctccgatgtc ggaaccggga accgctccga tggtcggctt cgcggccctc    660
atgcacgtcc tgccgcccgg gcgagcagtc ggagggagcg gcgcactgag tgctgcgttg    720
gcatcccgga tggctgtcga cggcgccacc gtcgcgctcg gtgacggcgt gacgtcgatc    780
cgccggaact cgaatcactg gaccgtcaca accgagagcg gtcgagaagt tcacgctcgc    840
aaggtaatcg cggggttgcca catcctcacg acactcgatc tcctgggcaa cggaggcttc    900
gaccgaacca cgctcgatca ctggcggcgg aagatcaggg tcggcccggg catcggcgct   960
gtattgcgac tggcgacatc tgcgctcccg tcctaccgcg gcgacgccac gacacgggaa    1020
agtacctcgg gattgcaatt actcgtttcc gatcgcgccc acttgcgcac tgcacacggc   1080
gcagcactgg caggggaact gcctcctcgc cctgcggttc tcggaatgag tttcagcgga    1140
atcgatccca cgatcgcccc ggccgggcgg catcaggtga cactgtggtc gcagtggcag   1200
ccgtatcgtc tcagcggaca tcgcgattgg gcgtcggtcg ccgaggccga ggccgaccgg   1260
atcgtcggcg agatgcaggc ttttgcaccc ggattcaccg attccgtcct cgaccgcttc   1320
attcaaactc cccgcgacat cgagtcggaa ttggggatga tcggcggaaa tgtcatgcac   1380
gtcgagatgt cactcgatca gatgatgttg tggcgaccgc ttcccgaact gtccggccat   1440
cgcgttccgg gagcagacgg gttgtatctg accggagcct cgacgcatcc cggtggtggt   1500
gtgtccggag ccagtggtcg cagtgccgct cgaatcgcac tgtccgacag ccgccggggt   1560
aaagcgagtc agtggatgcg tcgttcgagc aggtcgtga                           1599
```

<210> SEQ ID NO 8
<211> LENGTH: 1599
<212> TYPE: DNA
<213> ORGANISM: Rhodococcus erythropolis ATCC 47072

<400> SEQUENCE: 8

```
gtgagcgcgc ttctcgacgc cgtcgtcgtc ggctccggac acaacgcgct cgtatcggcc       60
gcctacctcg cacgcgaggg ttggtcggtc gaggttctgg agaaggacac ggttctcggc    120
ggcgccgtct cgaccgtcga gcgatttccc ggatacaagg tggaccgggg gtcgtcggca    180
cacctcatga tccgacacag cggcatcatc gaggaactcg gactcggcgc gcacggactg    240
cgctacatcg actgtgaccc gtgggcgttc gcgccgcccg ccccgggcac cgacgggccg   300
ggcatcgtgt tcaccgcga cctcgacgca acctgctggt ccatcgaacg agcatgcggg     360
acaaaggacg ccgactccta ccggcgattc gtcgcggtct ggtcggagcg cagtcgacat   420
gtcatgaaag cgttttccgc accgcccacc ggatcgaacc tgatcggtgc gttcggaggt   480
ctcgccaccg cacgcggcaa cagcgaactg tctcggcagt tcctcgcgcc tggcgacgca   540
ctgctcgacg agtatttcga cagtgaggca ctcaaagcag cgcttgcgtg gttcggcgcc  600
```

```
cagtccgggc ctgcgatgtc ggaaccggga accgctccga tggtcggctt cgcggccctc      660
atgcacgtct tgccgccagg gcgagcagtc ggtggaagcg gcgcactgag tgctgcgctg      720
gcctcccgga tggctgtcga cggcgccacg gtcgcgctcg gtgacggcgt gacgtcgatc      780
cgccgaaact cgagtcactg gaccgccaca accgagagcg gtcgagaagt tcacgctcgc      840
aaggtaatcg ccgggtgcca catcctgacc acgctcgatc tcctgggccg aggggcttc      900 gaccgaacca cgctcgatca ctggcggcgg aaaatcaggg tcggcccgg catcggcgcg       960 gtacttcgac tggcgacatc cgcgcttccg tcgtaccgcg gcgacgccac gacacgggaa     1020
agtacctcgg gattgcaatt actcgtctcc gatcgcgcac acttgcgcac tgcacacggc     1080
gcagcactgg cggggaact tcctcctcgc cctgcggttc tcggaatgag tttcagcgga      1140
atcgatccca cgatcgcccc ggccggtcgg catcaggtga cactgtggtc gcagtggcag     1200
ccgtatcgcc tcagcggaca tcgcgattgg gcatcggtcg ccgaggcgga ggccgaccgg     1260
atcgtcggcg agatggaggc tttcgcaccc gggttcgccg attccgtcct cgaccggttc     1320
attcagactc cccgggacat cgagtcggaa ttggggatga tcggcggaaa tgtcatgcac     1380
gtcgagatgt cactcgatca gatgatgttg tggcgaccgc ttccggaact gtccggccat     1440
cgcgttccgg gagcagacgg gttgtatctg accggagcat cgactcatcc cggtggcggt     1500
gtgtccggag ccagtggtcg cagtgcggct cgaatcgcac tgtcggacag ccgccggggc     1560
gcgactcgtc gttggatgcg tcgttcgagc aggtcgtga                            1599

<210> SEQ ID NO 9
<211> LENGTH: 18
<212> TYPE: DNA
<213> ORGANISM: artificial sequence
<220> FEATURE:
<223> OTHER INFORMATION: Primer

<400> SEQUENCE: 9
agcggcatca gcaccttg                                                     18

<210> SEQ ID NO 10
<211> LENGTH: 21
<212> TYPE: DNA
<213> ORGANISM: artificial sequence
<220> FEATURE:
<223> OTHER INFORMATION: Primer

<400> SEQUENCE: 10
gccaatatgg acaacttctt c                                                 21

<210> SEQ ID NO 11
<211> LENGTH: 28
<212> TYPE: DNA
<213> ORGANISM: artificial sequence
<220> FEATURE:
<223> OTHER INFORMATION: Primer

<400> SEQUENCE: 11
acctgaggtg ttcgacgagg acaaccga                                          28

<210> SEQ ID NO 12
<211> LENGTH: 28
<212> TYPE: DNA
<213> ORGANISM: artificial sequence
<220> FEATURE:
<223> OTHER INFORMATION: Primer
```

-continued

<400> SEQUENCE: 12
gttgcacagt ggtcatcgtg ccagccgt                                           28

<210> SEQ ID NO 13
<211> LENGTH: 11241
<212> TYPE: DNA
<213> ORGANISM: artificial sequence
<220> FEATURE:
<223> OTHER INFORMATION: Plasmid pRHBR17

<400> SEQUENCE: 13

| | | | | | |
|---|---|---|---|---|---|
| ttctcatgtt | tgacagctta | tcatcgataa | gctttaatgc | ggtagtttat | cacagttaaa | 60 |
| ttgctaacgc | agtcaggcac | cgtgtatgaa | atctaacaat | gcgctcatcg | tcatcctcgg | 120 |
| caccgtcacc | ctggatgctg | taggcatagg | cttggttatg | ccggtactgc | cgggcctctt | 180 |
| gcgggatatc | gtccattccg | acagcatcgc | cagtcactat | ggcgtgctgc | tagcgctata | 240 |
| tgcgttgatg | caatttctat | gcgcacccgt | tctcggagca | ctgtccgacc | gctttggccg | 300 |
| ccgcccagtc | ctgctcgctt | cgctacttgg | agccactatc | gactacgcga | tcatggcgac | 360 |
| cacacccgtc | ctgtggatcc | tctacgccgg | acgcatcgtg | gccggcatca | ccggcgccac | 420 |
| aggtgcggtt | gctggcgcct | atatcgccga | catcaccgat | ggggaagatc | gggctcgcca | 480 |
| cttcgggctc | atgagcgctt | gtttcggcgt | gggtatggtg | gcaggccccg | tggccggggg | 540 |
| actgttgggc | gccatctcct | tgcatgcacc | attccttgcg | gcggcggtgc | tcaacggcct | 600 |
| caacctacta | ctgggctgct | tcctaatgca | ggagtcgcat | aagggagagc | gtcgaccgat | 660 |
| gcccttgaga | gccttcaacc | cagtcagctc | cttccggtgg | gcgcggggca | tgactatcgt | 720 |
| cgccgcactt | atgactgtct | tctttatcat | gcaactcgta | ggacaggtgc | cggcagcgct | 780 |
| ctgggtcatt | ttcggcgagg | accgctttcg | ctggagcgcg | acgatgatcg | gcctgtcgct | 840 |
| tgcggtattc | ggaatcttgc | acgccctcgc | tcaagccttc | gtcactggtc | ccgccaccaa | 900 |
| acgtttcggc | gagaagcagg | ccattatcgc | cggcatggcg | gccgacgcgc | tgggctacgt | 960 |
| cttgctggcg | ttcgcgacgc | gaggctggat | ggccttcccc | attatgattc | ttctcgcttc | 1020 |
| cggcggcatc | gggatgcccg | cgttgcaggc | catgctgtcc | aggcaggtag | atgacgacca | 1080 |
| tcagggacag | cttcaaggat | cgctcgcggc | tcttaccagc | ctaacttcga | tcactggacc | 1140 |
| gctgatcgtc | acggcgattt | atgccgcctc | ggcgagcaca | tggaacgggt | tggcatggat | 1200 |
| tgtaggcgcc | gccctatacc | ttgtctgcct | ccccgcgttg | cgtcgcggtg | catggagccg | 1260 |
| ggccacctcg | acctgaatgg | aagccggcgg | cacctcgcta | acggattcac | cactccaaga | 1320 |
| attggagcca | atcaattctt | gcggagaact | gtgaatgcgc | aaaccaaccc | ttggcagaac | 1380 |
| atatccatcg | cgtccgccat | ctccagcagc | cgcacgcggc | gcatctcggg | cgcgttgct | 1440 |
| ggcgtttttc | cataggctcc | gccccctga | cgagcatcac | aaaaatcgac | gctcaagtca | 1500 |
| gaggtggcga | aacccgacag | gactataaag | ataccaggcg | tttccccctg | gaagctccct | 1560 |
| cgtgcgctct | cctgttccga | ccctgccgct | taccggatac | ctgtccgcct | ttctcccttc | 1620 |
| gggaagcgtg | gcgctttctc | atagctcacg | ctgtaggtat | ctcagttcgg | tgtaggtcgt | 1680 |
| tcgctccaag | ctgggctgtg | tgcacgaacc | ccccgttcag | cccgaccgct | gcgccttatc | 1740 |
| cggtaactat | cgtcttgagt | ccaacccggt | aagacacgac | ttatcgccac | tggcagcagc | 1800 |
| cactggtaac | aggattagca | gagcgaggta | tgtaggcggt | gctacagagt | tcttgaagtg | 1860 |
| gtggcctaac | tacggctaca | ctagaaggac | agtatttggt | atctgcgctc | tgctgaagcc | 1920 |
| agttaccttc | ggaaaaagag | ttggtagctc | ttgatccggc | aaacaaacca | ccgctggtag | 1980 |

```
cggtggtttt tttgtttgca agcagcagat tacgcgcaga aaaaaaggat ctcaagaaga    2040
tcctttgatc ttttctacgg ggtctgacgc tcagtggaac gaaaactcac gttaagggat    2100
tttggtcatg agattatcaa aaaggatctt cacctagatc cttttaaatt aaaaatgaag    2160
ttttaaatca atctaaagta tatatgagta aacttggtct gacagttacc aatgcttaat    2220
cagtgaggca cctatctcag cgatctgtct atttcgttca tccatagttg cctgactccc    2280
cgtcgtgtag ataactacga tacgggaggg cttaccatct ggccccagtg ctgcaatgat    2340
accgcgagac ccacgctcac cggctccaga tttatcagca ataaaccagc cagccggaag    2400
ggccgagcgc agaagtggtc ctgcaacttt atccgcctcc atccagtcta ttaattgttg    2460
ccgggaagct agagtaagta gttcgccagt taatagtttg cgcaacgttg ttgccattgc    2520
tgcaggcatc gtggtgtcac gctcgtcgtt tggtatggct tcattcagct ccggttccca    2580
acgatcaagg cgagttacat gatcccccat gttgtgcaaa aaagcggtta gctccttcgg    2640
tcctccgatc gttgtcagaa gtaagttggc cgcagtgtta tcactcatgg ttatggcagc    2700
actgcataat tctcttactg tcatgccatc cgtaagatgc ttttctgtga ctggtgagta    2760
ctcaaccaag tcattctgag aatagtgtat gcggcgaccg agttgctctt gcccggcgtc    2820
aacacgggat aataccgcgc cacatagcag aactttaaaa gtgctcatca ttggaaaacg    2880
ttcttcgggg cgaaaactct caaggatctt accgctgttg agatccagtt cgatgtaacc    2940
cactcgtgca cccaactgat cttcagcatc ttttactttc accagcgttt ctgggtgagc    3000
aaaaacagga aggcaaaatg ccgcaaaaaa gggaataagg gcgacacgga aatgttgaat    3060
actcatactc ttcctttttc aatattattg aagcatttat cagggttatt gtctcatgag    3120
cggatacata tttgaatgta tttagaaaaa taaacaaata ggggttccgc gcacatttcc    3180
ccgaaaagtg ccacctgacg tctaagaaac cattattatc atgacattaa cctataaaaa    3240
taggcgtatc acgaggccct ttcgtcttcg aataaatacc tgtgacggaa gatcacttcg    3300
cagaataaat aaatcctggt gtccctgttg ataccgggaa gccctgggcc aacttttggc    3360
gaaaatgaga cgttgatcgg cacgtaagag gttccaactt tcaccataat gaaataagat    3420
cactaccggg cgtatttttt gagttatcga gattttcagg agctaaggaa gctaaaatgg    3480
agaaaaaaat cactggatat accaccgttg atatatccca atggcatcgt aaagaacatt    3540
ttgaggcatt tcagtcagtt gctcaatgta cctataacca gaccgttcag attcagacca    3600
acaatcagtc caactagcaa ggcgacaacc ggtatcgcaa ttcgtgaaac aagctttgtc    3660
atgcgtccgc gctcttacga gcaggtgcgg agacggccgc tgcaggcatt ggaaccaaat    3720
tctccactgt gatggatagt gcgagacgat ccatgccagt catgtagggc tgcacccaga    3780
caaggccttc tgctcggtag atcgtgccga agctgaacgg ctcgttcggc gggttgatga    3840
cgtgcacgga tgctgtcttg tcagtcgcaa cagttccgtc cttgcgtgca actcggagca    3900
atgcgccagt cgaatacttc acacggccgt cgggagtgag cttgtcctga accggcttga    3960
tggggtcgtc cataccggct acgaacaccg ggaactgatc agcggtagtt gcgacgggga    4020
gggacgttcc gagctgaaca ttcatgcgag ttcctttgat cgaggctggt acagcttatg    4080
tctccggtgt ccatattcag cgacacgcgt tcatctacac tcaaaaccgt acacatagtg    4140
tagccagctg tccagttttc gcacactacg ttagcaactg aacatatttt gtggttgatc    4200
agtcaataag ctgtccatat ggacgagaaa gaggttcgcg cgatgattca gcgcaaagaa    4260
accgaacgaa aaatgcaggt catcaagcag gcgtccgtgg atctgtcaca ctcctggcag    4320
```

-continued

```
accattcaga acgcgcacga ctccacgact gtcgcaatgg agctacgaga agccgggctt    4380
caacgcgaat tctggctaca agctctcgcg gacatcacat ctgttgtggg aactgcctct    4440
gagctgcgca aatctatttc ccgtttctc gttgacgagc ttgacgtcag cagccgaacc    4500
gttgccaccg ttgcagatgt ttcaccgtcg accatcagta cttggcgtgg tgagcatgag    4560
tcatcgtaaa aacatcctct gacctgctat ggccccaatg atcacctatt accaaggcgg    4620
cggcttcgcc gccgctgcca gcaggctccc ccacctacgc gctccgcttc gctcgcgctt    4680
cggtgctccg cccgcaggcc caggagcgag tttgcgcctc gtttagtcca tctaaggggt    4740
tcctagctgg cttgaggtcg caacgcatcc tgaagtcgat cgaggagcag gaacgcatca    4800
tctcgatcca gcgtggtttc ttgaccataa atcgagaggt acacgcccat gacaacgcca    4860
tcgacgtcta ccgaagctgg attcgctgcg atgccaagag gacgttcgtt gatgctcatg    4920
tgatgggttt acctgcaaaa atagtcagca gccaaatcgg aggcggcggc ttcgccgccg    4980
ctgccagcag gctcccccac ctacgcgctc cgcttcgctc gcgcttcggt gctccgcccg    5040
caggcccagg agcgagtttg cgcctcgttt agtccatcta aggggttcct agctggcttg    5100
aggtcgcaac gcatcctgaa gtcgatcgag gagcaggaac gcatcatctc gatccagcgt    5160
ggtttcttga ccataaatcg agaggtacac gcccatgaca acgccatcga cgtctaccga    5220
agctggattc gctgcgatgc caagaggacg ttcgttgatg ctcatgtgat gggtttacct    5280
gcaaaaatag tcagcagcca aatcggccgg cctttttcta tctgcccggt cagccccccg    5340
agaccaacca tgaaacaggc cgtctctctg tcaaggccaa gccgctacgc ggtgctatcg    5400
cagccctgac agagagacac ccagcttcag agcggcaagt atcgggggga tgccctcaag    5460
tgtggttcat gcgggtgaaa gttgttgctc agcaacgctt ttcacttgcg aaccgatatt    5520
atcgggggcc gcacatccgc tgcgggcaat cgataatgca agtgatcacg aagatttttcc   5580
caagtcgcgc cagcttcgac gagtccgagg atctcgccga agacgtaagg cgcacaagtc    5640
cgaatcatca tccacgatcg cgccggaatg atcgcaacca tgaccggggc agattcttcc    5700
tgctcaacga tctgagcatc tgttagttct gccccaagac cagctcgggc acgcaatcca    5760
cgggaccacg cgattgcccg acgtcccatc gaaccaaact caaattctcg ccacagttcc    5820
aacgcttgtg gatccccgcc cactgcatca acagcgattt cccagggtgc acggttgcca    5880
tgtcgaccac ttttttccgtc gccactacca acctccatac caacgccaga tgcaattttc    5940
gtcagatacg cagcgagaac ttgatcagct tcaccgccga tctttcgtac atcgagacca    6000
cccgaattac gtagtggcgc agcaaatccc agagatacga gtttggaagt ccaccgatcg    6060
aacatcgcat ccgagaagga ttcgaggatg ttctcactca cgtcaccact gaacatgagt    6120
agcgcgtgaa cgtggacgtg ccagccgttt ttttccgtgag tgatttcaac agcgcgcacg    6180
tatccgtcgc agccgtacat ttcacgttcc gtacgccaac gacgaccgtt ggtcgcagct    6240
ttccaggctg ccgaaagtcc agtccatagg tcgtggagcc gctgaccagc tgtatggcgc    6300
atggtcatcg tcaccatcgc aacagatcca gtcccgagtt gatgagcaac aacttgagaa    6360
atttcgtctg cacgatgtgc accgactttt cccgcacagc aggggcagat ccagcccttt    6420
ccgcaggaac gaaggcctcc gaatccagaa cctttcggac cgttgacaat ggtcacaccg    6480
ttcacgccaa aaatcggccg gccacaggcg ttaaatgttt ctgacgtggt gatttgttga    6540
agtttgggtc gcagttcgtg ccggatgccg cgcttatcgg acgacacgag gacgggaggc    6600
cggtctttgc cggaaaggtg ttcagcactt acgctggtca taacgagcgg ggtcctagtc    6660
aagtaggagc ctcgaaggcg gcggcagggt ggtccaacac ccttcgtcgc cgctcgtatt    6720
```

```
ttcggagtaa atccagctag ttcagctcgg atactccact tcgaggttca tcgattattt    6780
ggtttttatc cacttaacca gcagaaacag cgtttatcgc tgatctgctg gtcagtgcgg    6840
cgtgtcgggg gagtcgctag tccgcggcga gtccccatgc ttcgagaaca ccgaccttct    6900
cttctgggt  tctgcttgtc ttcaccagtg catcgaacag acctcggtat tcacccaagt    6960
gttcaatatc gaatccggct tccctggcgt aatcagggt  gtagtagcag cacatcgcag    7020
ccagaatctc ggacgattcg gcgcgttcac cagcatgaat ccaaccataa acgtcatgcc    7080
caccccatag atcaggccct cgatgatcgt aaatgccaac ggctagtcgg aggatgaata    7140
ccgtagcttc gtgcttcacg catcaaccct ctgatctgct gcactcagaa ttgcatgacc    7200
tcccgaatga ctgcataact cgtcgtagac ctgagcaacg aacgaaggcc gatcagcatt    7260
gtccatgaag agttggacga acttcggccg gacgaggcca atccacggcg cagtcaaagt    7320
ttcaaaatca tgtgcctcga ggtgctcatg cattgcaacc gcccatgcgg ccctcgagc    7380
ggcgcaccag tctcgttcaa ctccctcgct gtccgaaatg tcgtatttaa ggcccagtga    7440
tcgtccaact tcggcagctg cgtcactggc acgtttccaa tcgtcaccgc gtaagtcgtt    7500
gagctttccg agttcatcgc ctagaagcag ctcagacatt gcaaaacgg  tcatcgaact    7560
gacccatcgt ggaccgacta gtgcaccaag gtcgtcgtcg gtgatctgca tgccgcgaag    7620
ttcgtcgacg acagcttggc cttccaaacc tactctggcc ctgagtattt cagttattac    7680
gagatgatcg ttcggccagc ctgatttgat ccggagtgca gtcgttacga ctcgttccgt    7740
gggcaggttt cggcgtgagg cgagttttc  tcctgcctca tgtgcaaacct tctcaaattg    7800
ctgtcgaatg taggtgttta ccgggattgc gtctgtcggg tagccgatca aggtgtgtcc    7860
tcctgtgtgt tcggttgtca gcctatgtcg ccgagatgtg ggtattccga ggcgattgtc    7920
attcgttgtg ctcggtcgat gttcagtgcg gcttcgtacg cgaggtctgc gttttcgacg    7980
taactcgcgt aggtcgagta ctcacctacg cgaaccgttc ggatcatttg gcgccgtagt    8040
ccgggttggt cgaagaagcc ttgaccaggg acgaatcctt cgaccagtgc gcactcttca    8100
ggtgttgcgt tggggtgcag catttttgaca gattcaggtt cgtctacgcg gagagtcatt    8160
ttcaccgcga agttcgagcg ggcgtttcca cccacgatgg aagcttccgc acgttgagcc    8220
aagagcaaca ttctgatgcc tgctttggca gactgagcag cgatctgtcg aacaagcgat    8280
gtgatgcggg gtgcgtatct gtctgctggt ttcagaccgt tggttgcatc gaaatcctgt    8340
gcgccctcga tgattccggg aaattcttcc agtacgagca ggatgagagg tagtgctggc    8400
gagaacaacg aaattttgtc tatgcgtcga tcccagaaac actcgattcg tcggtcagat    8460
tctgctttga cgaactggag cactcggagg actttgtcaa aatcgttcag cccgagctcg    8520
atgttcggtt cagccggtcg tcggtggacg aatgggcta  gtaagacgga agtgggatcg    8580
actccgacga cacgcacagc gggattcgat ccagcctgtg cgagcaggtt gtaggtgcat    8640
tgagattttc cggaacgggt tttgccttga atgagccagt gagcagcatc tttggctata    8700
tcgaccatga caggttgagc tagttcgttc catccaatcg caatcgggat cgtgtctgtt    8760
tgatccatca ggcgtccgtg ctttttgtcga acggaagatc cttttcttgc tcccaccagg    8820
gccgattgtc cccgagtatg ccgccggcct cttccttcaa tgtgccggcc gatgagtcct    8880
cgacgtcact gagccatgct gcatctcgtg cttgagaaat ggtgtctgca tcgatcagaa    8940
gtagctcgac ccgacgcggc tctactttgg tgaaactggc acgtagagca ccgaaagcat    9000
cggctatttt gaccgtcttc gatgtcatat cttcaccggt gatccctgtc ggaaggtcga    9060
```

```
aagcgactga tcgagtcaat ccgtcgtccg aaaatttgta gctacgaatg atgggaggct   9120
gcccagagga gttgatcaga ccaagattgg ccgcagcacc tgcaacttcc ggggttcctc   9180
gccaccatcg agctgtacga cgtttgcgac gccgagcctt cgttgcctct ctcaggtaga   9240
ccattgccac aacgcacacc agcagcacac tgaccaaaag ccacatctga gcgtcgaaga   9300
tgtacagcag cagaagcaac agaaacgtag aggacagaat cgggtaatcg gcaatttttg   9360
ccttgagttt tgctcgcaaa atttgccagg tggaacgtct tttaacctgg tcaccgcgtc   9420
gaacggcttc gtagttgctc atcggggcca ctccacaacg acattcggac tatctacttc   9480
gacttgctca tctacgttcc acaaccacga ttcgactgga acgagagcgc atcccgaggt   9540
tccattctga agattgcttt gcactcgatc actcatcaaa gtctctggaa ccgtctcagc   9600
ctctacgccc ttatgtaccg ggacaggggt attcacggtc aaatacactg cccgccagcc   9660
ctcaggcact ggcacgtcac cgcacgcgct ggtcttcgag tacggcgacg tgatgacctt   9720
tccatctggg ttagtccact ggatcccatc ggcgctcaat tccggattca ctcggatgta   9780
tccaggtatc tctctgcatg cactgacaga tggaacagaa cctgtcggaa gagggatct   9840 gcaccaggtc accgttcgtt cagcccatga gtcccgacgc tcttgcattc cgctggaaag   9900
cttaatatct tgcgtgccaa caatctggat attacggcct ttttaaagac cgtaaagaaa   9960
aataagcaca gttttatccc ggcctttatt cacattcttg cccgcctgat gaatgctcat   10020
ccggaattcc gtatggcaat gaaagacggt gagctggtga tatgggatag tgttcaccct   10080
tgttacaccg ttttccatga gcaaactgaa acgttttcat cgctctggag tgaataccac   10140
gacgatttcc ggcagtttct acacatatat tcgcaagatg tggcgtgtta cggtgaaaac   10200
ctggcctatt tccctaaagg gtttattgag aatatgtttt tcgtctcagc caatccctgg   10260
gtgagtttca ccagttttga tttaaacgtg gccaatatgg acaacttctt cgcccccgtt   10320
ttcaccatgg gcaaatatta tacgcaaggc gacaaggtgc tgatgccgct ggcgattcag   10380
gttcatcatg ccgtttgtga tggcttccat gtcggcagaa tgcttaatga attacaacag   10440
tactgcgatg agtggcaggg cggggcgtaa ttttttttaag gcagttattg gtgcccttaa   10500
acgcctggtg ctacgcctga ataagtgata ataagcggat gaatggcaga aattcgaaag   10560
caaattcgac ccggtcgtcg gttcagggca gggtcgttaa atagccgctt atgtctattg   10620
ctggtttacc ggtttattga ctaccggaag cagtgtgacc gtgtgcttct caaatgcctg   10680
aggccagttt gctcaggctc tccccgtgga ggtaataatt gacgatatga tcatttattc   10740
tgcctcccag agcctgataa aaacggtgaa tccgttagcg aggtgccgcc ggcttccatt   10800
caggtcgagg tggcccggct ccatgcaccg cgacgcaacg cggggaggca gacaaggtat   10860
agggcggcgc ctacaatcca tgccaacccg ttccatgtgc tcgccgaggc ggcataaatc   10920
gccgtgacga tcagcggtcc agtgatcgaa gttaggctgg taagagccgc gagcgatcct   10980
tgaagctgtc cctgatggtc gtcatctacc tgcctgaca gcatggcctg caacgcggc   11040 atcccgatgc cgccggaagc gagaagaatc ataatgggga aggccatcca gcctcgcgtc   11100
gcgaacgcca gcaagacgta gcccagcgcg tcggccgcca tgccggcgat aatggcctgc   11160
ttctcgccga aacgtttggt ggcgggacca gtgacgaagg cttgagcgag ggcgtgcaag   11220
attccgaata ccgcaagcga c                                             11241

<210> SEQ ID NO 14
<211> LENGTH: 1947
<212> TYPE: DNA
<213> ORGANISM: Rhodococcus erythropolis AN12
```

<400> SEQUENCE: 14

```
ttgggtgttc ttgcccgcat tcagggtcct gacgatctac gtcagttgag ccacgccgag        60
atgacggagt tggccgacga gattcgtgag ttcctcgtgc tgaaggtcgc tgcgaccggt       120
ggtcacctcg ggcccaactt gggcgtcgtg gagttgaccc tcgcactgca ccgaattttc       180
gactcgccgc aggacgcgat catcttcgac acgggccatc aggcctacgt gcacaagatc       240
ctcaccggtc gtcaggatca gttcgacact ctgcgtaagc agggcggact gtccgggtat       300
ccgtgccgcg ccgagagcga acacgactgg gtcgagtcct ctcacgcttc cgccgcgttg       360
tcctatgccg acggcctcgc gaaggccttc gcgctcacgg ccagaatcg ccacgttgtc        420
gccgtcgtcg gtgacggcgc cctgaccggc ggaatgtgtt gggaagccct caacaacatc       480
gcagccggaa aagaccgttc ggtggtgatc gtcgtcaacg acaacggccg ctcgtacgcg       540
ccgaccatcg gcggcctcgc cgaccatctt tcggcactgc gcaccgcgcc gagttacgag       600
cgcgccctcg acagtggccg acgcatggtc aagagactgc cctgggtggg gcgcaccgcg       660
tactccgtcc tgcacggaat gaaggcgggt ctcaaggacg ctgtcagccc tcaggtcatg       720
ttcaccgatc tgggtatcaa gtacctcgga ccggtcgacg gtcacgacga agccgccatg       780
gaatcggcgt tgcgccgggc gaaggcctac ggcggaccgg tcatcgttca tgccgtcact       840
cgtaagggca acgttacgc acacgccgag aacgacgtgg ccgaccagat gcatgccacc        900
ggcgtcatcg atcccgtcac cggtcgcggc accaagtcgt ccgcgccgga ctggacgtcg       960
gtcttctcgg ccgcattgat cgagcaggct tcgcgtcgtg aggacattgt cgccatcacc      1020
gcggcgatgg ccgggcccac cggcctcgcg gccttcgggg agaagttccc cgatcggatt      1080
ttcgacgtcg gtatcgccga gcagcatgcg atgacctcgg ccgccggtct tgcacttggc      1140
ggacttcacc ccgtcgttgc tatctactcg accttcctca atcgggcttt cgaccagttg      1200
ttgatggacg tcgcactgct caaacaaccg gtgacagtcg tgctcgaccg cgccggggtc      1260
accggagtcg acggcgccag ccacaacggc gtctgggatc tttcgctgct cggaatcatc      1320
ccggggattc gcgtcgcggc accgcgtgat gcagacacac tgcgggaaga gttggacgag      1380
gcgcttctcg tcgacgacgg cccaacggtc gtacggttcc cgaagggtgc tgtacccgaa      1440
gcgattccgg cagtgaagcg actcgacgga atggtcgacg tcctcaaggc cagcgagggt      1500
gagcgcggcg acgtgctcct cgtcgcggtg ggcccatttg catccttggc gctcgagatt      1560
gccgagcggc tcgacaagca gggcatctcg gttgccgtcg ttgatccgcg atgggttctg      1620
ccggtcgcgg attcgctggt gaagatggcg gacaagtacg ccctcgtggt caccatcgaa      1680
gacgcgggtt tgcacggcgg catcggttcg acggtctcgg ccgcgatgcg tgccgccgga      1740
gtgcacacgt cgtgccgcga catgggcgtt ccccagcagt tcctcgatca cgccagccgc      1800
gaagccatcc acaaggaact cggactcacg gctcaggacc tctcccgcaa gatcaccggc      1860
tgggtggcgg ggatgggcag cgtcggcgtc cacgtccagg aagacgcgtc ctcggcttcg      1920
gctcagggcg aagtcgcgca aggctga                                          1947
```

<210> SEQ ID NO 15
<211> LENGTH: 20
<212> TYPE: DNA
<213> ORGANISM: artificial sequence
<220> FEATURE:
<223> OTHER INFORMATION: Primer

<400> SEQUENCE: 15

US 7,186,523 B2
45                                                              46
-continued

```
atttcgttga acggctcgcc                                                        20

<210> SEQ ID NO 16
<211> LENGTH: 20
<212> TYPE: DNA
<213> ORGANISM: artificial sequence
<220> FEATURE:
<223> OTHER INFORMATION: Primer

<400> SEQUENCE: 16
cggcaatccg acctctacca                                                        20

<210> SEQ ID NO 17
<211> LENGTH: 20
<212> TYPE: DNA
<213> ORGANISM: artificial sequence
<220> FEATURE:
<223> OTHER INFORMATION: Primer

<400> SEQUENCE: 17
tgagacgagc cgtcagcctt                                                        20

<210> SEQ ID NO 18
<211> LENGTH: 1554
<212> TYPE: DNA
<213> ORGANISM: Brevibacterium linens ATCC 9175
<220> FEATURE:
<221> NAME/KEY: CDS
<222> LOCATION: (1)..(1554)

<400> SEQUENCE: 18 atg aca cag aga cgc cgg ccc aga gat cgc ttc gcc gag aga atc cag            48
Met Thr Gln Arg Arg Arg Pro Arg Asp Arg Phe Ala Glu Arg Ile Gln
1               5                   10                  15 ggc ccg cag gga cgg ccg cga ctg ctt cga ccc aaa cgg gtc acc atc            96
Gly Pro Gln Gly Arg Pro Arg Leu Leu Arg Pro Lys Arg Val Thr Ile
            20                  25                  30 atc ggc gcc ggc atc gcc gga ctg gct gca gcc gcg att ttg gcc gaa           144
Ile Gly Ala Gly Ile Ala Gly Leu Ala Ala Ala Ala Ile Leu Ala Glu
        35                  40                  45 cac ggc gcc gag gtc acg gtc atc gag aag acc gac tac ctc ggc ggc           192
His Gly Ala Glu Val Thr Val Ile Glu Lys Thr Asp Tyr Leu Gly Gly
    50                  55                  60 cga gtg ggc gcc tgg ccg gtc gac gac gaa cgg acc atg agc cga gga           240
Arg Val Gly Ala Trp Pro Val Asp Asp Glu Arg Thr Met Ser Arg Gly
65                  70                  75                  80 ttc cac gcc ttc ttc cgg cag tac tac aac ctg cgc gac ctg ctc agc           288
Phe His Ala Phe Phe Arg Gln Tyr Tyr Asn Leu Arg Asp Leu Leu Ser
                85                  90                  95 cgc gca gat ccc gaa ggt gaa tgc ctg cgg ccc gtc gac gac tac ccg           336
Arg Ala Asp Pro Glu Gly Glu Cys Leu Arg Pro Val Asp Asp Tyr Pro
            100                 105                 110 ctc atc cat cgc cga ggc tcg atg gac acg ttc gcc tca att ccc cgc           384
Leu Ile His Arg Arg Gly Ser Met Asp Thr Phe Ala Ser Ile Pro Arg
        115                 120                 125 acc ccg ccg ttc aat ctc ctc ggt ttc gtc tgg cag agc ccc acc ttc           432
Thr Pro Pro Phe Asn Leu Leu Gly Phe Val Trp Gln Ser Pro Thr Phe
    130                 135                 140 ccg atc aga gga ctc cgc gac gtc gat atc gct gcc gca gtc gaa ctc           480
Pro Ile Arg Gly Leu Arg Asp Val Asp Ile Ala Ala Ala Val Glu Leu
145                 150                 155                 160 atc gac gtc gag ttc ccc gca acg tac agc tac tat gac ggc gaa tct           528
Ile Asp Val Glu Phe Pro Ala Thr Tyr Ser Tyr Tyr Asp Gly Glu Ser
```

```
                    165                 170                 175
gcc gcc gac ttc ctc gac cgg ttg cgc ttt ccc gac gaa gcc cgc cat      576
Ala Ala Asp Phe Leu Asp Arg Leu Arg Phe Pro Asp Glu Ala Arg His
            180                 185                 190 ctg gcg ctc gaa gtc ttc gcc cgc tcc ttc ttc gcc gac ccg aca gag      624
Leu Ala Leu Glu Val Phe Ala Arg Ser Phe Phe Ala Asp Pro Thr Glu
        195                 200                 205 ttc tct gcg ggt gag ctc gtg gcc atg ttc cac acc tac ttc acc ggt      672
Phe Ser Ala Gly Glu Leu Val Ala Met Phe His Thr Tyr Phe Thr Gly
    210                 215                 220 tca gcg gaa ggg ctg ctc ttc gac gtc ccc gtc gat gac tac gac aca      720
Ser Ala Glu Gly Leu Leu Phe Asp Val Pro Val Asp Asp Tyr Asp Thr
225                 230                 235                 240 gct cta tgg gca ccg ttg ggc ggc tac ctc gag tca ctg ggg gtc acg      768
Ala Leu Trp Ala Pro Leu Gly Gly Tyr Leu Glu Ser Leu Gly Val Thr
                245                 250                 255 atc gag acg ggg acg acc gtg acc tcg atc gat ccc acc gag tcc gga      816
Ile Glu Thr Gly Thr Thr Val Thr Ser Ile Asp Pro Thr Glu Ser Gly
            260                 265                 270 tgg acg acc acg acc gga gag gcg aac ctg gaa agt gat gcc gtc gtg      864
Trp Thr Thr Thr Thr Gly Glu Ala Asn Leu Glu Ser Asp Ala Val Val
        275                 280                 285 ctc gca gtc gat cct gcc gct gcc cgc gat ctg ctc agc gca agc cat      912
Leu Ala Val Asp Pro Ala Ala Ala Arg Asp Leu Leu Ser Ala Ser His
    290                 295                 300 gac tcg ctc gtg gac agc gca ccc gcg gcc caa cgg tgg atg gag acg      960
Asp Ser Leu Val Asp Ser Ala Pro Ala Ala Gln Arg Trp Met Glu Thr
305                 310                 315                 320 atc ggc tca cag acc aac gct ccc gcg ttc gca gtg ctg cga ctg tgg     1008
Ile Gly Ser Gln Thr Asn Ala Pro Ala Phe Ala Val Leu Arg Leu Trp
                325                 330                 335 ctc ggc acg ccc gtg gcc gac cac cga ccg gcc ttc ctg ggg aca agc     1056
Leu Gly Thr Pro Val Ala Asp His Arg Pro Ala Phe Leu Gly Thr Ser
            340                 345                 350 ggg tac gac ctc ctt gac aac gtg tcc gta ctt gag cgc ttc gag gcc     1104
Gly Tyr Asp Leu Leu Asp Asn Val Ser Val Leu Glu Arg Phe Glu Ala
        355                 360                 365 gga gcc aga gcg tgg tcc gaa tcc cac cac ggt tcg gtc ctc gaa ctc     1152
Gly Ala Arg Ala Trp Ser Glu Ser His His Gly Ser Val Leu Glu Leu
    370                 375                 380 cac gct tat gcc ctt gaa ggc gat tca tac gac acc gag cgt ggg agg     1200
His Ala Tyr Ala Leu Glu Gly Asp Ser Tyr Asp Thr Glu Arg Gly Arg
385                 390                 395                 400 gcg gac atc gtt gcg cgg ctt ctg tca gat ctg cat cac gtc tac ccc     1248
Ala Asp Ile Val Ala Arg Leu Leu Ser Asp Leu His His Val Tyr Pro
                405                 410                 415 gaa acc gca gcc ctg acc atc gtt gac cag gag ctg ctc atc gaa gcg     1296
Glu Thr Ala Ala Leu Thr Ile Val Asp Gln Glu Leu Leu Ile Glu Ala
            420                 425                 430 gac tgc ggt ctt act gac acc cgc ccg tgg gag gac agg ccc gag ccg     1344
Asp Cys Gly Leu Thr Asp Thr Arg Pro Trp Glu Asp Arg Pro Glu Pro
        435                 440                 445 tcc acc ccg atc ccc ggg ctg gtg gtc gcc gga gac tat gtg cgc tgc     1392
Ser Thr Pro Ile Pro Gly Leu Val Val Ala Gly Asp Tyr Val Arg Cys
    450                 455                 460 aat acc cct gtg gcc ttg atg gaa cgt gcc gcc acg act ggt tat ctg     1440
Asn Thr Pro Val Ala Leu Met Glu Arg Ala Ala Thr Thr Gly Tyr Leu
465                 470                 475                 480 gcc gcc aac cac ctg ctc tct acc tgg agg gtc gag ggg acg gac ctg     1488
```

```
Ala Ala Asn His Leu Leu Ser Thr Trp Arg Val Glu Gly Thr Asp Leu
            485                 490                 495 tgg tcg cca ccg acc cga ggc ctg ctt cgg cgt gga gtg ctc ggg ctc      1536
Trp Ser Pro Pro Thr Arg Gly Leu Leu Arg Arg Gly Val Leu Gly Leu
        500                 505                 510 atc agg aga cgt cga tga                                               1554
Ile Arg Arg Arg Arg
        515

<210> SEQ ID NO 19
<211> LENGTH: 517
<212> TYPE: PRT
<213> ORGANISM: Brevibacterium linens ATCC 9175

<400> SEQUENCE: 19

Met Thr Gln Arg Arg Pro Arg Asp Arg Phe Ala Glu Arg Ile Gln
1               5                   10                  15

Gly Pro Gln Gly Arg Pro Arg Leu Leu Arg Pro Lys Arg Val Thr Ile
            20                  25                  30

Ile Gly Ala Gly Ile Ala Gly Leu Ala Ala Ala Ile Leu Ala Glu
        35                  40                  45

His Gly Ala Glu Val Thr Val Ile Glu Lys Thr Asp Tyr Leu Gly Gly
    50                  55                  60

Arg Val Gly Ala Trp Pro Val Asp Asp Glu Arg Thr Met Ser Arg Gly
65                  70                  75                  80

Phe His Ala Phe Phe Arg Gln Tyr Tyr Asn Leu Arg Asp Leu Leu Ser
                85                  90                  95

Arg Ala Asp Pro Glu Gly Glu Cys Leu Arg Pro Val Asp Asp Tyr Pro
            100                 105                 110

Leu Ile His Arg Arg Gly Ser Met Asp Thr Phe Ala Ser Ile Pro Arg
        115                 120                 125

Thr Pro Pro Phe Asn Leu Leu Gly Phe Val Trp Gln Ser Pro Thr Phe
    130                 135                 140

Pro Ile Arg Gly Leu Arg Asp Val Asp Ile Ala Ala Ala Val Glu Leu
145                 150                 155                 160

Ile Asp Val Glu Phe Pro Ala Thr Tyr Ser Tyr Tyr Asp Gly Glu Ser
                165                 170                 175

Ala Ala Asp Phe Leu Asp Arg Leu Arg Phe Pro Asp Glu Ala Arg His
            180                 185                 190

Leu Ala Leu Glu Val Phe Ala Arg Ser Phe Phe Ala Asp Pro Thr Glu
        195                 200                 205

Phe Ser Ala Gly Glu Leu Val Ala Met Phe His Thr Tyr Phe Thr Gly
    210                 215                 220

Ser Ala Glu Gly Leu Leu Phe Asp Val Pro Val Asp Tyr Asp Thr
225                 230                 235                 240

Ala Leu Trp Ala Pro Leu Gly Gly Tyr Leu Glu Ser Leu Gly Val Thr
                245                 250                 255

Ile Glu Thr Gly Thr Thr Val Thr Ser Ile Asp Pro Thr Glu Ser Gly
            260                 265                 270

Trp Thr Thr Thr Thr Gly Glu Ala Asn Leu Glu Ser Asp Ala Val Val
        275                 280                 285

Leu Ala Val Asp Pro Ala Ala Arg Asp Leu Leu Ser Ala Ser His
    290                 295                 300

Asp Ser Leu Val Asp Ser Ala Pro Ala Ala Gln Arg Trp Met Glu Thr
305                 310                 315                 320
```

```
Ile Gly Ser Gln Thr Asn Ala Pro Ala Phe Ala Val Leu Arg Leu Trp
            325                 330                 335
Leu Gly Thr Pro Val Ala Asp His Arg Pro Ala Phe Leu Gly Thr Ser
        340                 345                 350
Gly Tyr Asp Leu Leu Asp Asn Val Ser Val Leu Glu Arg Phe Glu Ala
    355                 360                 365
Gly Ala Arg Ala Trp Ser Glu Ser His His Gly Ser Val Leu Glu Leu
370                 375                 380
His Ala Tyr Ala Leu Glu Gly Asp Ser Tyr Asp Thr Glu Arg Gly Arg
385                 390                 395                 400
Ala Asp Ile Val Ala Arg Leu Leu Ser Asp Leu His Val Tyr Pro
                405                 410                 415
Glu Thr Ala Ala Leu Thr Ile Val Asp Gln Glu Leu Leu Ile Glu Ala
            420                 425                 430
Asp Cys Gly Leu Thr Asp Thr Arg Pro Trp Glu Asp Arg Pro Glu Pro
        435                 440                 445
Ser Thr Pro Ile Pro Gly Leu Val Ala Gly Asp Tyr Val Arg Cys
    450                 455                 460
Asn Thr Pro Val Ala Leu Met Glu Arg Ala Ala Thr Thr Gly Tyr Leu
465                 470                 475                 480
Ala Ala Asn His Leu Leu Ser Thr Trp Arg Val Glu Gly Thr Asp Leu
                485                 490                 495
Trp Ser Pro Pro Thr Arg Gly Leu Leu Arg Arg Gly Val Leu Gly Leu
            500                 505                 510
Ile Arg Arg Arg Arg
        515
```

<210> SEQ ID NO 20
<211> LENGTH: 24
<212> TYPE: DNA
<213> ORGANISM: artificial sequence
<220> FEATURE:
<223> OTHER INFORMATION: Primer

<400> SEQUENCE: 20
gtgctcatgc tgtggcagtg gcaa                                          24

<210> SEQ ID NO 21
<211> LENGTH: 31
<212> TYPE: DNA
<213> ORGANISM: artificial sequence
<220> FEATURE:
<223> OTHER INFORMATION: Primer

<400> SEQUENCE: 21
tcatcgacgt ctcctgatga gcccgagcac t                                  31

<210> SEQ ID NO 22
<211> LENGTH: 1176
<212> TYPE: DNA
<213> ORGANISM: artificial sequence
<220> FEATURE:
<223> OTHER INFORMATION: Chloramphenicol resistance marker

<400> SEQUENCE: 22
gtgcctttcg ctatctacgt cctcgggctt gccgtctttg cccagggcac atccgaattc    60
atgttgtccg gctcatacc ggatatggcc cgcgacctcg cgtctcggt ccccgccgcc    120 ggactcctca cctcgccctt cgcggtcggg atgatcatcg cgctccgct gatggccatc    180

```
gccagcatgc ggtggcccg gcgacgcgcc cttttgacat tcctcatcac gttcatgctg      240
gtccacgtca tcggcgcgct caccagcagc ttcgaggtct tgctggtcac acgcatcgtc      300
ggcgccctcg ccaacgccgg attcttggcg gtggccctgg gcgcggcgat ggcgatggtg      360
cccgccgaca tgaaagggcg cgcaacgtcc gtcctcctcg gtggtgtcac gatcgcatgt      420
gtagccggag ttcccggggg cgccttcctc ggtgaaatat ggggctggcg tgcagcgttc      480
tgggctgtcg tcgtcatctc cgcccctgcg gtggtggcga tcatgttcgc cacccggcc       540 gagccgccag cagagtccac accgaacgcc aagcgtgaac tgtcctcgct gcgctcacgc      600
aagctccagc tgatgcttgt cctcggtgcc ctgatcaacg gcgcaacatt ctgttcgttc      660
acctacatgg cgcccactct caccgacatc tccggtttcg actcccgttg gattccgttg      720
ctgctggggt tgttcgggct cggatcgttc atcggcgtca gcgtcggagg caggctcgcc      780
gatacccggc cgttccaact tctcgccgtg ggatccgcag cactgttgac gggatggatc      840
gtcttcgctc tcacggcatc ccaccctgcg gtgacattgg tgatgctgtt cgtgcagggc      900
gctctgtcct tcgcggtcgg ctcgaccttg atctcccagg tgctctacgc cgccgacgcg      960
gcgccgacct tgggtggatc gttcgcgacg gccgcgttca acgtcggcgc tgcactgggc     1020
ccggccctcg gcgggctggc gatcggtatg ggcctgagct accgcgcccc gctctggacg     1080
agcgccgcgc tggtgactct cgcgatcgtc atcggcgcag ccaccttgtc gctctggcgg     1140
cgtccagcgt ccgtccagga aaccgtccca gcctga                               1176
```

```
<210> SEQ ID NO 23
<211> LENGTH: 26
<212> TYPE: DNA
<213> ORGANISM: artificial sequence
<220> FEATURE:
<223> OTHER INFORMATION: Primer

<400> SEQUENCE: 23
ccatggcgaa gtaccgtcac gtgcac                                           26

<210> SEQ ID NO 24
<211> LENGTH: 32
<212> TYPE: DNA
<213> ORGANISM: artificial sequence
<220> FEATURE:
<223> OTHER INFORMATION: Primer

<400> SEQUENCE: 24
ccatggcaat tgtcaggctg ggacggtttc ct                                    32
```

METHOD FOR SYNTHESIS OF ARYL-CAROTENOIDS

This application claims the benefit of U.S. Provisional Application No. 60/378,312, filed May 6, 2002.

FIELD OF THE INVENTION

This invention is in the field of microbiology. More specifically, this invention pertains to a method for microbial production of aryl-carotenoid compounds.

BACKGROUND OF THE INVENTION

Carotenoids are pigments that are ubiquitous throughout nature and synthesized by all photosynthetic organisms, and in some heterotrophic growing bacteria and fungi. Carotenoids provide color for flowers, vegetables, insects, fish and birds. Colors of carotenoids range from yellow to red with variations of brown and purple. As precursors of vitamin A, carotenoids are fundamental components in our diet and they play an important role in human health. Industrial uses of carotenoids include pharmaceuticals, food supplements, animal feed additives, and colorants in cosmetics, to mention a few.

Because animals are unable to synthesize carotenoids de novo, they must obtain them by dietary means. Thus, manipulation of carotenoid production and composition in plants or bacteria can provide new or improved sources for carotenoids.

Carotenoids come in many different forms and chemical structures. Most naturally occurring carotenoids are hydrophobic tetraterpenoids containing a $C_{40}$ methyl-branched hydrocarbon backbone derived from successive condensation of eight $C_5$ isoprene units (IPP). In addition, novel carotenoids with longer or shorter backbones occur in some species of nonphotosynthetic bacteria. Carotenoids exhibit great variations and may be acyclic, monocyclic, or bicyclic depending on whether the ends of the hydrocarbon backbones have been cyclized to yield aliphatic or cyclic ring structures (G. Armstrong, (1999) In *Comprehensive Natural Products Chemistry*, Elsevier Press, volume 2, pp 321–352).

Carotenoid biosynthesis starts with the isoprenoid pathway to generate the $C_5$ isoprene unit, isopentenyl pyrophosphate (IPP). IPP is then condensed with its isomer dimethylallyl pyrophosphate (DMAPP) to generate the $C_{10}$ geranyl pyrophosphate (GPP) which is then elongated to form the $C_{15}$ farnesyl pyrophosphate (FPP). FPP synthesis is common in both carotenogenic and non-carotenogenic bacteria. Additional enzymes in the carotenoid pathway are able to then generate carotenoid pigments from the FPP precursor, segregating into two categories: (i) carotene backbone synthesis enzymes and (ii) subsequent modification enzymes. The backbone synthesis enzymes include geranyl geranyl pyrophosphate synthase, phytoene synthase, phytoene dehydrogenase, and lycopene cyclase, etc. The modification enzymes include ketolases, hydroxylases, dehydratases, glycosylases, etc.

It is known that β-carotene can be converted to isorenieratene by the carotene desaturase. The crtU gene, encoding the carotene desaturase, has been identified in a few actinomycetes including *Streptomyces*, *Mycobacterium* and *Brevibacterium* (Krugel et al., *Biochimica et Biophysica Acta*, 1439: 57–64 (1999); Krubasik and Sandmann, *Mol Gen Genet*, 263: 423–432 (2000); and Viveiros et al., *FEMS Microbiol Lett*, 187: 95–101 (2000)). Another aryl-carotene, chlorobactene, was reported in photosynthetic green bacteria (Liaaen-Jensen et al., *Acta Chem. Scand*, 18: 1703–1718 (1964); Takaichi et al., *Arch Microbiol*, 168: 270–276 (1997)). Recent genomic sequencing of *Chlorobium tepidum* identified a putative carotene desaturase gene (Eisen et al., *PNAS USA*, 99: 9509–9514 (2002), which might be responsible for the synthesis of the native chlorobactene and derivatives. However, function of the putative carotene desaturase gene from *Chlorobium* has not yet been determined. It is likely that the CrtU from actinomycetes might also act on other substrates in addition to β-carotene to produce a variety of aryl-carotenoids, such as converting γ-carotene to chlorobactene. However, previous attempts to express crtU in heterologous hosts have not been successful (Schumann et al., *Mol Gen Genet*, 252: 658–666 (1996)). The inability to express the carotene desaturase in a heterologous host is unfortunate and presents a significant hurdle to the synthesis of a variety of aryl-carotenoids by genetic engineering. Furthermore, natural aryl-carotenoids are always present as mixtures of the aryl-carotenoid with their precursors or derivatives (Kohl et al., *Phytochemistry*, 22: 207–213 (1983); Takaichi et al., supra). Production of a pure aryl-carotenoid requires the ability to express the carotene desaturase in a heterologous host.

The problem to be solved is to express a functional carotene desaturase (crtU) gene for the production of aryl-carotenoids in a heterologous host. Applicants have solved the stated problem by isolating the crtU gene from *Brevibacterium linens* and expressing the gene from a plasmid in the *Rhodococcus erythropolis* ATCC 47072 strain.

SUMMARY OF THE INVENTION

The invention provides methods for the production of aryl carotenoid compounds by the bioconversion of cyclic carotenoid substrates in the presence of a carotene desaturase. Specifically the invention provides a method for the production of aryl carotenoid compounds comprising:
(a) providing a host cell which comprises a cyclic carotenoid having at least one β-ionone ring;
(b) transforming the host cell of (a) with a gene encoding a carotene desaturase; and
(c) growing the transformed host cell of (b) under conditions whereby an aryl carotenoid is produced.

Additionally the invention provides a method of regulating aryl carotenoid biosynthesis in an host cell comprising:
(a) introducing into a host cell a carotene desaturase gene encoding an polypeptide having the amino acid sequence as set forth in SEQ ID NO:19 under the control of suitable regulatory sequences; and
(b) growing the host cell of (a) under conditions whereby the carotene desaturase gene is expressed and aryl carotenoid biosynthesis is regulated.

In a preferred embodiment the invention provides a method for the production of isorenieratene comprising:
(a) providing a host cell which comprises β-carotene;
(b) transforming the host cell of (a) with a gene encoding a carotene desaturase; and
(c) growing the transformed host cell of (b) under conditions whereby an aryl carotenoid is produced.

In another preferred embodiment the invention provides a method for the production of chlorobactene comprising:
(a) providing a host cell which comprises γ-carotene;
(b) transforming the host cell of (a) with a gene encoding a carotene desaturase; and
(c) growing the transformed host cell of (b) under conditions whereby an aryl carotenoid is produced.

BRIEF DESCRIPTION OF THE DRAWINGS AND SEQUENCE DESCRIPTIONS

Figure 5:
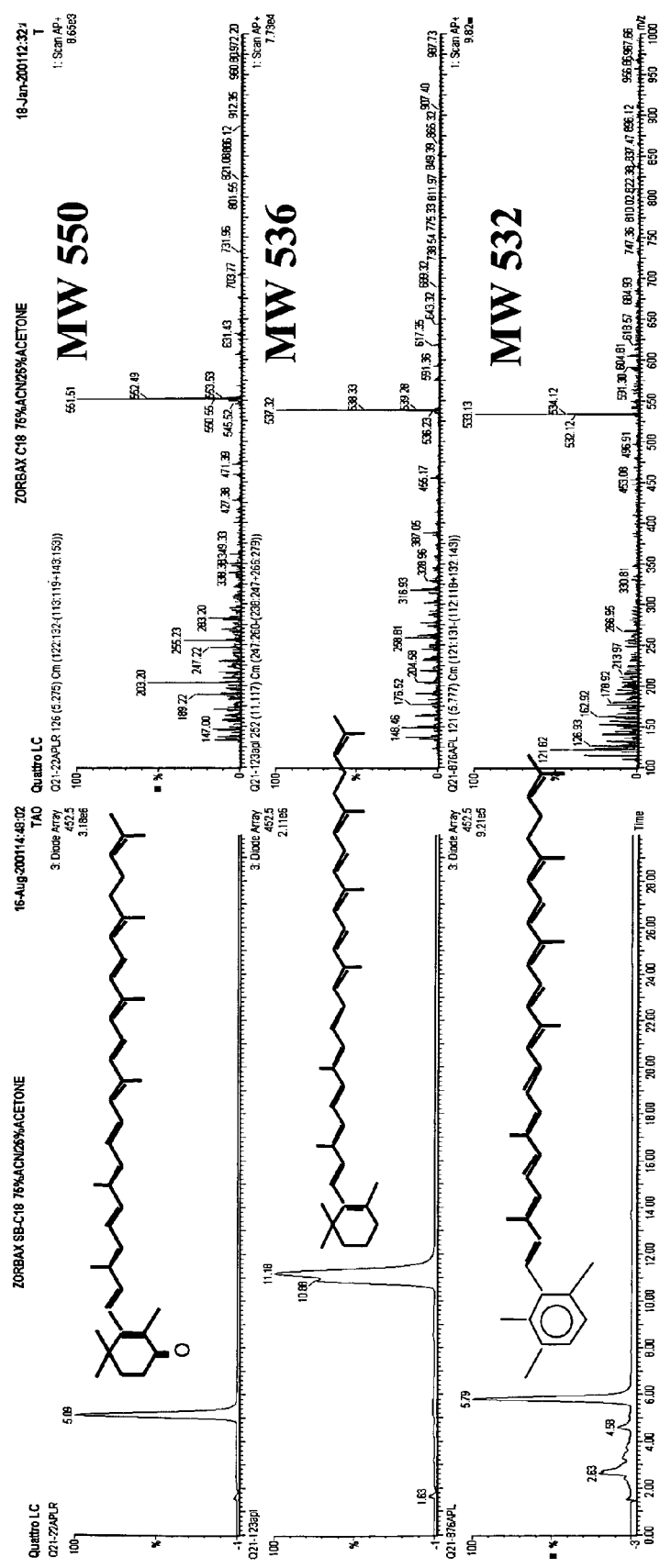

FIG. 5 describes LC/MS analysis of carotenoids synthesized by recombinant *Rhodococcus* strains.

Figure 6:
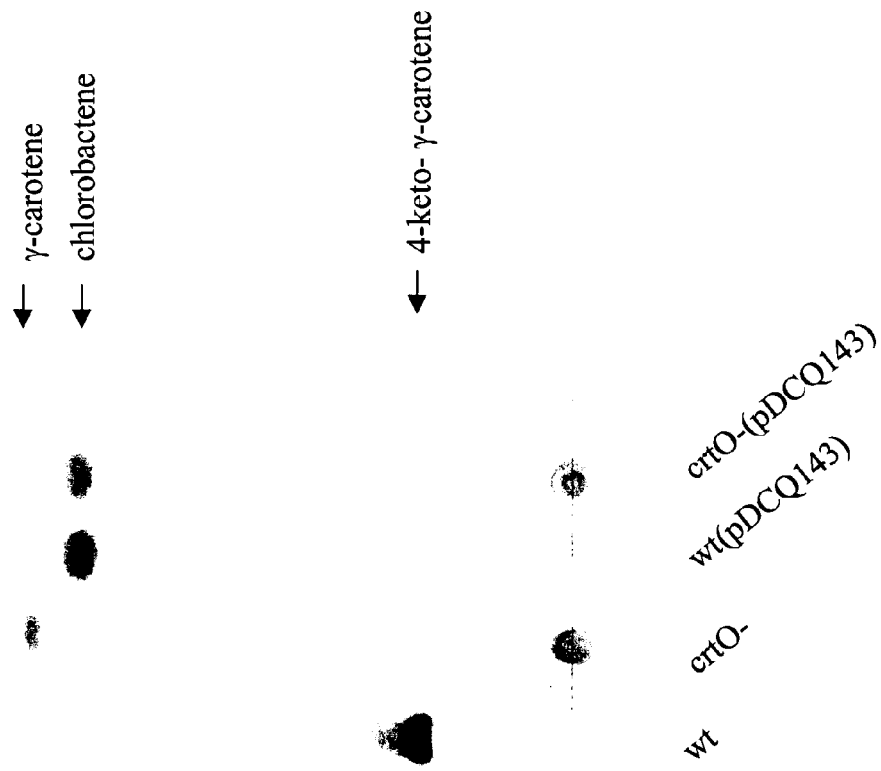

FIG. 6 is a TLC analysis of carotenoids produced in *Rhodococcus* strains.

The invention can be more fully understood from the following detailed description and the accompanying sequence descriptions, which for a part of this application.

The following sequences comply with 37 C.F.R. 1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1–3 are oligonucleotide primers used to amplify 16s rRNA.

SEQ ID NO:4 is the nucleotide sequence for the 16s rRNA gene from *Rhodococcus erythropolis* AN12.

SEQ ID NOs:5–6 are oligonucleotide primers designed to amplify the crtO gene.

SEQ ID NO:7 is the nucleotide sequence for the *Rhodococcus erythropolis* AN12 crtO gene.

SEQ ID NO:8 is the nucleotide sequence for the *Rhodococcus erythropolis* ATCC 47072 crtO gene.

SEQ ID NOs:9–10 are oligonucleotide primers designed to amplify pBR328 sequence.

SEQ ID NOs:11–12 are oligonucleotide primers designed to amplify crtO from ATCC 47072.

SEQ ID NO:13 is the nucleotide sequence for the pRHBR17 *E. coli-Rhodococcus* shuttle plasmid.

SEQ ID NO:14 is the nucleotide sequence for the dxs gene of *Rhodococcus erythropolis* AN12.

SEQ ID NOs:15–17 are oligonucleotide primers used to amplify dxs from AN12.

SEQ ID NO:18 is the nucleotide sequence of the crtU gene from *Brevibacterium linens* ATCC 9175 with GenBank® Accession number AF139916.

SEQ ID NO:19 is the amino acid sequence of CrtU from *Brevibacterium linens* ATCC 9175 with GenBank® Accession number AF139916.

SEQ ID NOs:20 and 21 are primers used for the amplification of the crtU gene.

SEQ ID NO:22 is the nucleotide sequence of a chloramphenicol resistance marker with the GenBank® Accession number AJ 308376.

SEQ ID NOs:23 and 24 are primers used to amplify and isolate the chloramphenicol resistance marker as defined by SEQ ID NO:22.

DETAILED DESCRIPTION OF THE INVENTION

The present invention provides a method for the conversion of cyclic carotenoids having a β-ionone ring to the corresponding aryl carotenoid, via the heterologous expression of a carotene desaturase gene (crtU).

The expression of crtU in a heterologous host is useful for the production of aryl carotenoids individually, as well as for the regulation and production of other carotenoids in the isoprenoid biosynthetic pathway. There is a general practical utility for microbial production of carotenoid compounds as these compounds are very difficult to make chemically (Nelis and Leenheer, *Appl. Bacteriol.*, 70:181–191 (1991)). Introduction of the aromatic ring(s) may possibly render the carotenoids more stable, which would be desired for certain applications such as uses for food colorants In this disclosure, a number of terms and abbreviations are used for the interpretation of the claims and the specification.

"Open reading frame" is abbreviated ORF.

"Polymerase chain reaction" is abbreviated PCR.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The terms "isoprenoid" or "terpenoid" refer to the compounds derived from the isoprenoid pathway including 10 carbon terpenoids and their derivatives, such as carotenoids and xanthophylls.

The terms "*Rhodococcus erythropolis* AN12" or "AN12" are used interchangeably and refer to the *Rhodococcus erythropolis* AN12 strain.

The terms "*Rhodococcus erythropolis* ATCC 47072" or "ATCC 47072" are used interchangeably and refer to the *Rhodococcus erythropolis* ATCC 47072 strain.

The term "carotenoid" refers to a compound composed of a polyene backbone which is condensed from five-carbon isoprene unit. Carotenoids can be acyclic or terminated with one (monocyclic) or two (bicyclic) cyclic end groups. The term "carotenoid" may include both carotenes and xanthophylls. A "carotene" refers to a hydrocarbon carotenoid. Carotene derivatives that contain one or more oxygen atoms, in the form of hydroxy-, methoxy-, oxo-, epoxy-, carboxy-, or aldehydic functional groups, or within glycosides, glycoside esters, or sulfates, are collectively known as "xanthophylls". Carotenoids that are particularly suitable in the present invention are monocyclic and bicyclic carotenoids.

The term "carotene desaturase" refers to the group of enzymes that can desaturate and transfer methyl or other groups of the β-ionone ring of mono- or bi-cyclic carotenoids. A preferred carotene desaturase for use herein is the crtU isolated from *Brevibacterium linens* ATCC 9175 and having the amino acid sequence as set forth in SEQ ID NO:19.

Figure 1:
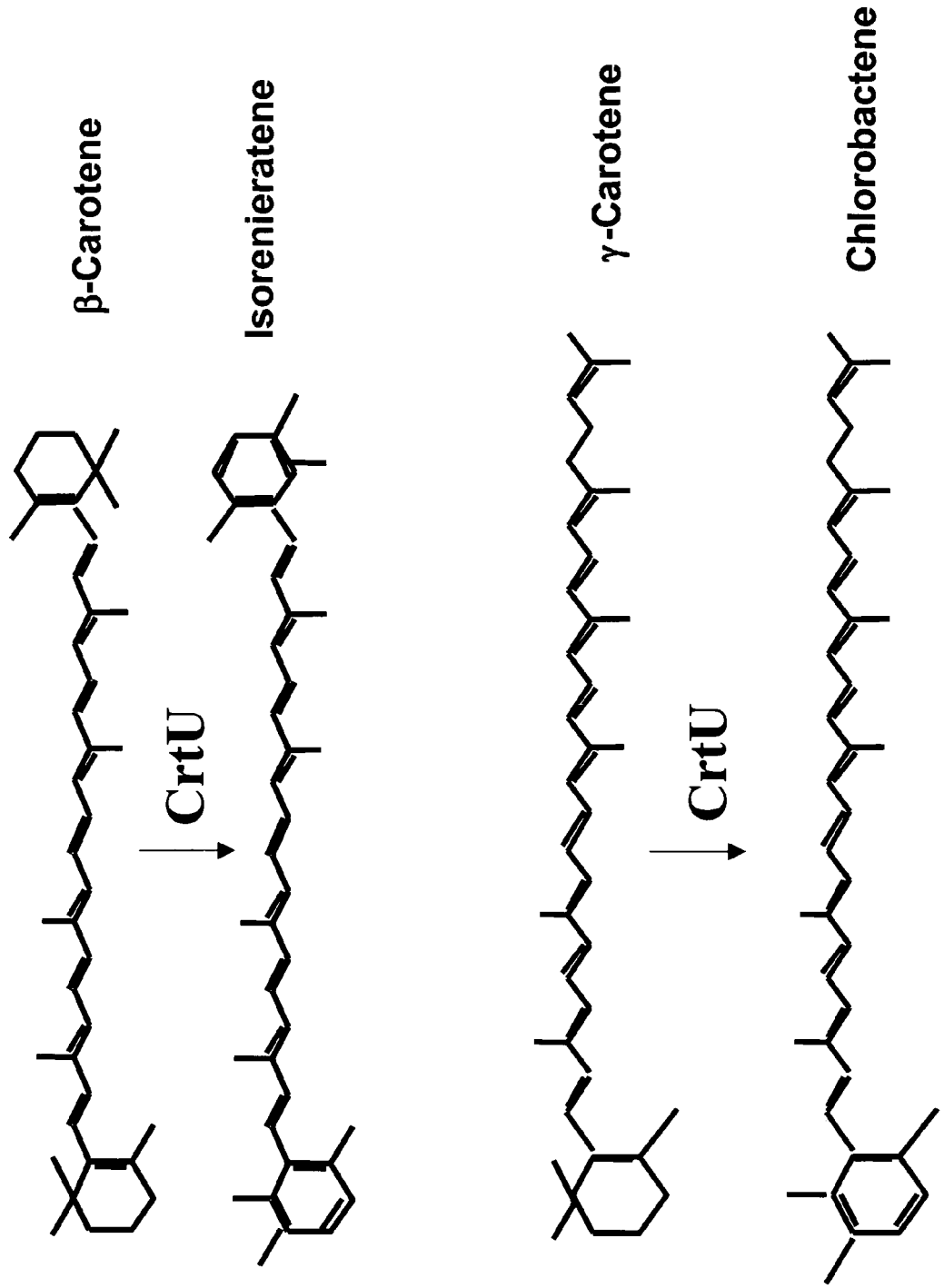
FIG. 1 illustrates the enzymatic aromatization of carotenoids by CrtU.

The term "aryl-carotenoid" refers to carotenoids with at least one aromatic end group, including isorenieratene, β-isorenieratene, chlorobactene, and derivates as shown in FIG. 1.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 9928508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", "vector", and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

The present invention provides a method for the in vivo biotransformation of cyclic carotenes having a β-ionone ring to the corresponding aryl carotenoid. The method proceeds by expressing a heterologous gene encoding a carotene desaturase (crtU) enzyme in a host cell that produces a suitable cyclic carotene substrate, where the β-ionone ring is aromatized to produce the corresponding aryl carotenoid.

Carotene Desaturase Activity

Biosynthesis of aromatic carotenoids catalyzed by CrtU proceeds by desaturation and methyltransferation of the β-ionone ring of the cyclic carotenoids (Krugel et al., supra). CrtU, expressed in its native host, has been shown to convert β-carotene (two β-ionone rings) to aromatic groups of isorenieratene in *Streptomyces griseus, Brevibacterium linens* and *Mycobacterium auraum A+* (Krugel et al., supra; Krubasik and Sandmann, supra; Viveiros et al., supra).

A number of carotene desaturases are known and will be suitable in the present invention. For example, carotene desaturase has been identified in *Streptomyces avermitilis* (GenBank® Accession No. AB070934) *Streptomyces griseus*, (GenBank® Accession No. AF272737), *Mycobacterium aurum*, (GenBanke® Accession No. AJ133724), *Brevibacterium linens* (GenBank® Accession No. AF139916), and *Streptomyces coelicolor* (GenBank® Accession No. AL109989) and AL109962, and microbial genome database gnl |TIGR| *M. avium* 89, *Chlorobium tepidum* TLS (CyanoBase CT0323), where the carotene desaturase isolated from *Brevibacterium linens* as described by SEQ ID NO:19 is preferred.

The preferred substrate for carotene desaturase is a cyclic carotene having at least one β-ionone ring. Typical suitable substrates include, but are not limited to, β-carotene; γ-carotene; α-carotene; zeaxanthin; β-isorenieratene (φ,β-carotene); torulene; 1'2'-dihydro-γ-carotene; 7, 8-dihydro-γ-carotene; 7'8'-dihydro-β-carotene; 7',8',7,8-tetrahydro-β-carotene; β-zeacarotene; echinenone; 3-OH-β-carotene; 1',2'-dihydro-1'-OH-torulene; 16'-OH-torulene; 16'-oxo-torulene; and 16'-carboxy-torulene.

Typical aryl carotenoids that will be produced by the aromatization of the β-ionone ring on the cyclic carotenoid will include, but are not limited to isorenieratene (φ,φ-carotene); β-isorenieratene (φ,β-carotene); chlorobactene (φ,ψ-carotene); φ,ε-carotene; 1,2-didehydrochlorobactene; 1',2'-dihydrochlorobactene; 7,8-dihydro-chlorobactene; 7'8'-dihydro-isorenieratene; 7',8',7,8-tetrahydro-isorenieratene; 7'8'-dihydro-chlorobactene; β,φ-carotene-4-one; β,φ-carotene-3-ol; 3-OH-isorenieratene; 3, 3'-dihydroxy-isorenieratene; 7', 8'-didehydrorenieratene; OH-chlorobactene; 1',2'-dihydro-1'-OH-didehydrochlorobactene; 16'-OH-didehydrochlorobactene; 16'-oxo-didehydrochlorobactene; and 16'-carboxy-didehydrochlorobactene. Aryl carotenoids of the invention may be either symmetrical (having two β-ionone rings) as with β-carotene for example, or may be asymmetrical having only a single β-ionone ring as with γ-carotene for example.

Within the context of the present invention a preferred substrate is β-carotene which is catalyzed to isorenieratene or γ-carotene which is catalyzed to chlorobactene by the action of the crtU gene product.

Recombinant Expression—Microbial

A gene encoding a carotene desaturase (crtU) has been expressed recombinantly in a heterologous microbial host. Expression of crtU in recombinant microbial hosts will be useful for the synthesis of new products heretofore not possible using the native host.

Preferred heterologous host cells for expression of the instant genes and nucleic acid fragments are microbial hosts that can be found broadly within the fungal or bacterial families and which grow over a wide range of temperature, pH values, and solvent tolerances. For example, it is contemplated that any of bacteria, yeast, and filamentous fungi will be suitable hosts for expression of the present crtU genes.

It will be appreciated by the skilled artisan that the expression of the present crtU genes may be regulated by controlling a number of well known factors. For example, large-scale microbial growth and functional gene expression may utilize a wide range of simple or complex carbohydrates, organic acids and alcohols, and saturated hydrocarbons, such as methane or carbon dioxide, in the case of photosynthetic or chemoautotrophic hosts. However, the functional genes such as crtU may be regulated, repressed or depressed by specific growth conditions, which may include the form and amount of nitrogen, phosphorous, sulfur, oxygen, carbon or any trace micronutrient including small inorganic ions. In addition, the regulation of crtU genes may be achieved by the presence or absence of specific regulatory molecules that are added to the culture and are not typically considered nutrient or energy sources. Growth rate may also be an important regulatory factor in gene expression.

A variety of microbial host cells will be suitable for the heterologous expression of the present crtU. Examples of host strains include but are not limited to bacterial, fungal or yeast species such as *Aspergillus, Trichoderma, Saccharo-*

*myces, Pichia, Candida, Rhodotorula, Rhodosporidium, Phaffia, Hansenula,* or bacterial species such as *Salmonella, Bacillus, Acinetobacter, Zymomonas, Agrobacterium, Erythrobacter Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella,* and *Myxococcus.*

Microbial expression systems and expression vectors containing regulatory sequences that direct high level expression of foreign proteins are well known to those skilled in the art. Any of these could be used to construct chimeric genes for expression of present carotene desaturase. These chimeric genes could then be introduced into appropriate microorganisms via transformation to provide high-level expression of the enzymes.

Accordingly, it is expected that introduction of chimeric gene encoding the instant bacterial enzymes under the control of the appropriate promoters will result in the production of aryl carotenoids or in the modulation of an existing isoprenoid pathway.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the instant ORF's in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, $IP_L$, $IP_R$, T7, tac, and trc (useful for expression in *Escherichia coli*) as well as the amy, apr, and npr promoters and various phage promoters useful for expression in *Bacillus*.

Termination control regions may also be derived from various genes native to the preferred hosts. Optionally, a termination site may be unnecessary, however, it is most preferred if included.

Knowledge of the sequence of the present gene will be useful in manipulating the isoprenoid or carotenoid biosynthetic pathways in any organism having such a pathway. Methods of manipulating genetic pathways are common and well known in the art. Selected genes in a particularly pathway may be upregulated or down regulated by variety of methods. Additionally, competing pathways organism may be eliminated or sublimated by gene disruption and similar techniques.

Once a key genetic pathway has been identified and sequenced specific genes may be upregulated to increase the output of the pathway. For example, additional copies of the targeted genes may be introduced into the host cell on multicopy plasmids such as pBR322. Alternatively, the target genes may be modified so as to be under the control of non-native promoters. Where it is desired that a pathway operate at a particular point in a cell cycle or during a fermentation run, regulated or inducible promoters may used to replace the native promoter of the target gene. Similarly, in some cases the native or endogenous promoter may be modified to increase gene expression. For example, endogenous promoters can be altered in vivo by mutation, deletion, and/or substitution (see, Kmiec, U.S. Pat. No. 5,565, 350; Zarling et al., PCT/US93/03868).

Alternatively, it may be necessary to reduce or eliminate the expression of certain genes in the target pathway or in competing pathways that may serve as competing sinks for energy or carbon. Methods of down-regulating genes for this purpose have been explored. Where sequence of the gene to be disrupted is known, one of the most effective methods gene down regulation is targeted gene disruption where foreign DNA is inserted into a structural gene so as to disrupt transcription. This can be effected by the creation of genetic cassettes comprising the DNA to be inserted (often a genetic marker) flanked by sequence having a high degree of homology to a portion of the gene to be disrupted. Introduction of the cassette into the host cell results in insertion of the foreign DNA into the structural gene via the native DNA replication mechanisms of the cell. (See for example Hamilton et al., *J. Bacteriol.*, 171:4617–4622 (1989), Balbas et al., *Gene*, 136:211–213 (1993), Gueldener et al., *Nucleic Acids Res.*, 24:2519–2524 (1996), and Smith et al., *Methods Mol. Cell. Biol.*, 5:270–277 (1996)).

Antisense technology is another method of down regulating genes where the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA which encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down regulating genes where the sequence is known, other less specific methodologies have been developed that are not sequence based. For example, cells may be exposed to a UV radiation and then screened for the desired phenotype. Mutagenesis with chemical agents is also effective for generating mutants and commonly used substances include chemicals that affect nonreplicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. See for example Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.*, 36, 227, (1992).

Another non-specific method of gene disruption is the use of transposable elements or transposons. Transposons are genetic elements that insert randomly in DNA but can be latter retrieved on the basis of sequence to determine where the insertion has occurred. Both in vivo and in vitro transposition methods are known. Both methods involve the use of a transposable element in combination with a transposase enzyme. When the transposable element or transposon is contacted with a nucleic acid fragment in the presence of the transposase, the transposable element will randomly insert into the nucleic acid fragment. The technique is useful for random mutageneis and for gene isolation, since the disrupted gene may be identified on the basis of the sequence of the transposable element. Kits for in vitro transposition are commercially available (see, for example, The Primer Island Transposition Kit, available from Perkin Elmer Applied Biosystems, Branchburg, N.J., based upon the yeast Ty1 element; The Genome Priming System, available from New England Biolabs, Beverly, Mass.; based upon the bacterial transposon Tn7; and the EZ::TN Transposon Insertion Systems, available from Epicentre Technologies, Madison, Wis., based upon the Tn5 bacterial transposable element).

Within the context of the present invention, where there is a pre-existing isoprenoid pathway in the selected host cell, it will be useful, for example to disrupt the gene encoding the ketolase encoded by crtO. This, because the gene product of crtO competes with crtU for the same substrate, and disruption of crtO will be expected to enhance the enzymatic product of crtU (see FIG. 2).

Industrial Production

Where commercial production of aryl-carotenoid compounds is desired using the present crtU genes, a variety of culture methodologies may be applied. For example, large-scale production of a specific gene product overexpressed from a recombinant microbial host may be produced by both batch and continuous culture methodologies.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch culturing methods are common and well known in the art and examples may be found in Brock (supra) and Deshpande (supra).

Commercial production of aryl-carotenoids may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively, continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, methane or methanol for which metabolic conversion into key biochemical intermediates has been demonstrated. In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415–32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.*, 153:485–489 (1990)). Hence it is contemplated that the source of carbon utilized in the present invention may encompass a wide variety of carbon containing substrates and will only be limited by the choice of organism.

Recombinant Expression—Plants

Plants and algae are also known to produce carotenoid compounds. The crtU genes of the instant invention may be used to create transgenic plants having the ability to express a carotene desaturase. Preferred plant hosts will be any variety that will support a high production level of this enzyme. Suitable green plants will include but are not limited to soybean, rapeseed (*Brassica napus, B. campestris*), pepper, sunflower (*Helianthus annus*), cotton (*Gossypium hirsutum*), corn, tobacco (*Nicotiana tabacum*), alfalfa (*Medicago sativa*), wheat (*Triticum* sp), barley (*Hor-* deum vulgare), oats (Avena sativa, L), sorghum (Sorghum bicolor), rice (Oryza sativa), Arabidopsis, cruciferous vegetables (broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees, and forage grasses. Algal species include, but are not limited to, commercially significant hosts such as *Spirulina, Haemotacoccus,* and *Dunalliela.* Production of the aryl carotenoid compounds may be accomplished by first constructing chimeric genes of present invention in which the coding region are operably linked to promoters capable of directing expression of a gene in the desired tissues at the desired stage of development. For reasons of convenience, the chimeric genes may comprise promoter sequences and translation leader sequences derived from the same genes. 3' Non-coding sequences encoding transcription termination signals must also be provided. The instant chimeric genes may also comprise one or more introns in order to facilitate gene expression.

Any combination of promoter and terminator capable of inducing expression of a coding region may be used in the chimeric genetic sequence. Some suitable examples of promoters and terminators include those from nopaline synthase (nos), octopine synthase (ocs) and cauliflower mosaic virus (CaMV) genes. One type of efficient plant promoter that may be used is a high-level plant promoter. Such promoters, in operable linkage with the genetic sequences of the present invention, should be capable of promoting expression of the present gene product. High-level plant promoters that may be used in this invention include the promoter of the small subunit (ss) of the ribulose-1,5-bisphosphate carboxylase from soybean (Berry-Lowe et al., *J. Molecular and App. Gen.,* 1:483–498 (1982)), and the promoter of the chlorophyll a/b binding protein. These two promoters are known to be light-induced in plant cells (see, for example, *Genetic Engineering of Plants, an Agricultural Perspective,* A. Cashmore, Plenum, N.Y. (1983), pages 29–38; Coruzzi, G. et al., *The Journal of Biological Chemistry,* 258:1399 (1983), and Dunsmuir, P. et al., *Journal of Molecular and Applied Genetics,* 2:285 (1983)).

Plasmid vectors comprising the instant chimeric genes can then constructed. The choice of plasmid vector depends upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., *EMBO J.,* 4:2411–2418 (1985); De Almeida et al., *Mol. Gen. Genetics,* 218:78–86 (1989)), and thus multiple events must be screened in order to obtain lines displaying the desired expression level and pattern. Such screening may be accomplished by Southern analysis of DNA blots (Southern, *J. Mol. Biol.* 98:503 (1975)), Northern analysis of mRNA expression (Kroczek, J., *Chromatogr. Biomed. Appl.,* 618 (1–2):133–145 (1993)), and Western analysis of protein expression, or phenotypic analysis.

For some applications it will be useful to direct the instant proteins to different cellular compartments. It is thus envisioned that the chimeric genes described above may be further supplemented by altering the coding sequences to encode enzymes with appropriate intracellular targeting sequences such as transit sequences (Keegstra, K., *Cell,* 56:247–253 (1989)), signal sequences or sequences encoding endoplasmic reticulum localization (Chrispeels, J. J., *Ann. Rev. Plant Phys. Plant Mol. Biol.,* 42:21–53 (1991)), or nuclear localization signals (Raikhel, N., *Plant Phys.,* 100: 1627–1632 (1992)) added and/or with targeting sequences that are already present removed. While the references cited give examples of each of these, the list is not exhaustive and more targeting signals of utility may be discovered in the future that are useful in the invention.

Cells comprising a carotene desaturase (crtU) enzyme maybe harvested and crude cell extracts prepared by means well known in the art. Alternatively, the crtU enzyme may be purified by ion exchange, hydroxyapatite, ammonium sulfate, sizing gel, and PAGE gel electrophoresis chromatography using standard techniques.

Crude cell extracts or purified protein may be suspended in a buffer and contacted with a carotenoid substrate (having a β-ionone ring) dissolved in a suitable solvent such as acetone. These reactants may be mixed and incubated for suitable time and the reaction stopped by solvent extraction of the carotenoid products.

DESCRIPTION OF THE PREFERRED EMBODIMENTS

Figure 2:
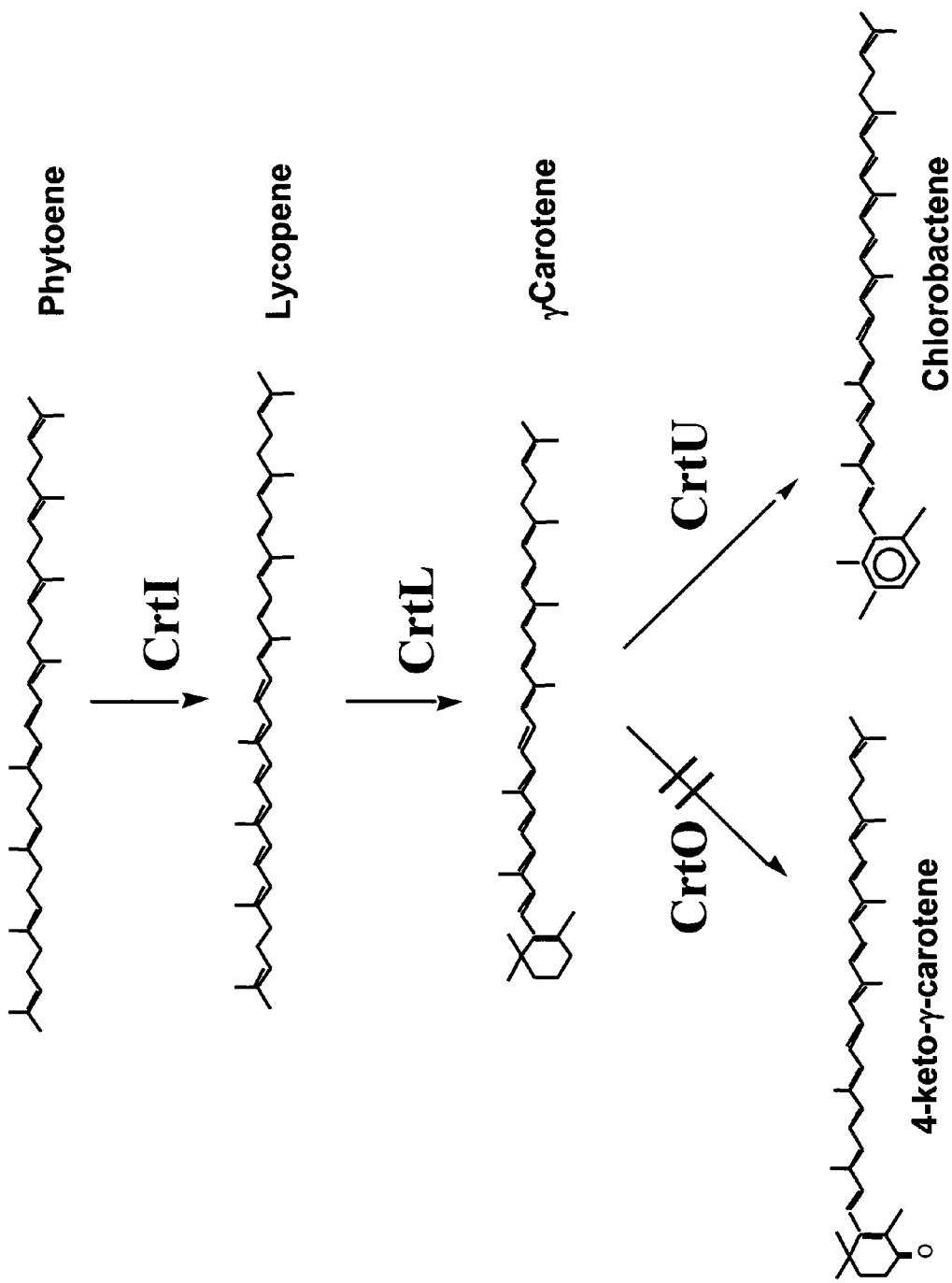
FIG. 2 illustrates the strategy for synthesis of aryl-carotenoids in *Rhodococcus erythropolis* ATCC 47072.

The present crtU gene and its expression product, CrtU, a carotene desaturase, is useful for the creation of recombinant organisms that have the ability to produce aryl-carotenoid compounds. Nucleic acid fragments encoding CrtU have been isolated from a strain of *Brevibacterium linens* and expressed in *Rhodococcus erythropolis* ATCC 47072. The *Rhodococcus erythropolis* ATCC 47072 naturally produces 4-keto-γ-carotene as the major carotenoid, and CrtO was identified to be the carotenoid ketolase responsible for converting γ-carotene to 4-keto-γ-carotene (FIG. 2). Because biosynthesis of aromatic carotenoids catalyzed by CrtU proceeds by desaturation and methyltransferation of the β-ionone rings of carotenoids, either β-carotene or γ-carotene are potential substrates. To make a β-ionone ring structure available for the CrtU, the natural CrtO activity was removed from the strain by a knockout mutation. In one example, the crtU gene from *B. linens* was expressed with the *Rhodococcus* dxs gene (encoding 1-deoxyxylulose-5-phosphate synthase) which was used to improve flux of isoprenoid pathway metabolites. In another example, the crtU gene was expressed using the chloramphenicol resistance gene promoter, which improved expression levels.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual;* Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F.

M. et al., Current Protocols in Molecular Biology, pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Brock, supra. All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences were accomplished using the suite of programs available from the Genetics Computer Group Inc. (Wisconsin Package Version 9.0, Genetics Computer Group (GCG), Madison, Wis.). Where the GCG program "Pileup" was used the gap creation default value of 12, and the gap extension default value of 4 were used. Where the CGC "Gap" or "Bestfit" programs were used the default gap creation penalty of 50 and the default gap extension penalty of 3 were used. Multiple alignments were created using the FASTA program incorporating the Smith-Waterman algorithm (W. R. Pearson, *Comput. Methods Genome Res.,* [Proc. Int. Symp.] (1994), Meeting Date 1992, 111–20. Editor(s): Suhai, Sandor. Publisher: Plenum, New York, N.Y.). In any case where program parameters were not prompted for, in these or any other programs, default values were used.

The meaning of abbreviations is as follows: "h" means hour(s), "min" means minute(s), "sec" means second(s), "d" means day(s), "mL" means milliliters, "µL" means microliters, "L" means liters, "µg" means micrograms, "mM" means millimolar, "µM" means micromolar, "ppm" means parts per million, and "nm" means nanometer.

Bacterial Strains

Bacterial strains used in the following examples and their sources are given in the table below:

| Bacterial Strain | Use | Source |
| --- | --- | --- |
| *Rhodococcus erythropolis* ATCC 47072 | Production of chlorobactene | American Type Culture Collection P.O. Box 1549 Manassas, VA 20108, U.S.A |
| *Rhodococcus erythropolis* AN12 | Source of crtO, dxs genes | Example 1 |
| *Brevibacterium linens* ATCC 9175 | Source of crtU gene | American Type Culture Collection P.O. Box 1549 Manassas, VA 20108, U.S.A |

Vectors

Transformation and expression vectors used in the following examples and their sources are given in the table below:

| Vector Designation | Purpose | Source/description |
| --- | --- | --- |
| pCR2.1 TOPO | Sub-cloning vector | Invitrogen Carlsbad, CA |
| pBR328 | Used as an integration vector to create *Rhodococcus* crtO knockout strain | American Type Culture Collection #37517 P.O. Box 1549 Manassas, VA 20108, U.S.A (Genbank Accession #L08858) |
| pDA71 | *E. coli-Rhodococcus* shuttle vector | American Type Culture Collection #77474 P.O. Box 1549 Manassas, VA 20108, U.S.A |
| pDCQ102 | pBR328(crtO *R. erythropolis* ATCC 47072) | Example 2 |
| pRhBR17 | *E. coli-Rhodococcus* shuttle vector | Example 3 |
| pRhBR171 | *E. coli-Rhodococcus* shuttle vector | Example 3 |
| pDCQ22 | pRhBR171(dxs *R. erythropolis* AN12) | Example 3 |
| pDCQ23 | pRhBR171(dxs *R. erythropolis* AN12) | Example 3 |
| pDCQ138 | pCR2.1(*B. linens* crtU) | Example 4 |
| pDCQ139 | pDCQ23(*B. linens* crtU) | Example 4 |
| pDCQ140 | pDA71(dxs-crtU) | Example 4 |
| pDCQ141 | pCR2.1(cmR) | Example 5 |
| pDCQ142 | pRhBR171(cmR) | Example 5 |
| pDCQ143 | PDCQ142(crtU) | Example 5 |

Example 1

Isolation and Characterization of Strain AN12

This Example describes the isolation of strain AN12 of *Rhodococcus erythropolis* on the basis of being able to grow on aniline as the sole source of carbon and energy. Analysis of a 16S rRNA gene sequence indicated that strain AN12 was related to high G+C Gram positive bacteria belonging to the genus *Rhodococcus*.

Bacteria that grow on aniline were isolated from an enrichment culture. The enrichment culture was established by inoculating 1 mL of activated sludge into 10 mL of S12 medium (10 mM ammonium sulfate, 50 mM potassium phosphate buffer (pH 7.0), 2 mM $MgCl_2$, 0.7 mM $CaCl_2$, 50 µM $MnCl_2$, 1 µM $FeCl_3$, 1 µM $ZnCl_3$, 1.72 µM $CuSO_4$, 2.53 µM $CoCl_2$, 2.42 µM $Na_2MoO_2$, and 0.0001% $FeSO_4$) in a 125 mL screw cap Erlenmeyer flask. The activated sludge was obtained from a wastewater treatment facility. The enrichment culture was supplemented with 100 ppm aniline added directly to the culture medium and was incubated at 25° C. with reciprocal shaking. The enrichment culture was maintained by adding 100 ppm of aniline every 2–3 days. The culture was diluted every 14 days by replacing 9.9 mL of the culture with the same volume of S12 medium. Bacteria that utilize aniline as a sole source of carbon and energy were isolated by spreading samples of the enrichment culture onto S12 agar. Aniline was placed on the interior of each petri dish lid. The petri dishes were sealed with parafilm and incubated upside down at room temperature (25° C.). Representative bacterial colonies were then tested for the ability to use aniline as a sole source of carbon and energy. Colonies were transferred from the original S12 agar plates used for initial isolation to new S12 agar plates and supplied with aniline on the interior of each petri dish lid. The petri dishes were sealed with parafilm and incubated upside down at room temperature (25° C.).

The 16S rRNA genes of each isolate were amplified by PCR and analyzed as follows. Each isolate was grown on R2A agar (Difco Laboratories, Bedford, Mass.). Several colonies from a culture plate were suspended in 100 µL of water. The mixture was frozen and then thawed. The 16S rRNA gene sequences were amplified by PCR by using a commercial kit according to the manufacturer's instructions (Perkin Elmer, Boston, Mass.) with primers HK12 (5'-GAGTTTGATCCTGGCTCAG-3') (SEQ ID NO:1) and HK13 (5'-TACCTTGTTACGACTT-3') (SEQ ID NO:2). PCR was performed in a Perkin Elmer GeneAmp 9600. The samples were incubated for 5 minutes at 94° C. and then cycled 35 times at 94° C. for 30 seconds, 55° C. for 1 minute, and 72° C. for 1 minute. The amplified 16S rRNA genes were purified using a commercial kit according to the manufacturer's instructions (QIAquick PCR Purification Kit, Qiagen, Valencia, Calif.) and sequenced on an automated ABI sequencer. The sequencing reactions were initiated with primers HK12, HK13, and HK14 (5'-GTGCCAG-CAGYMGCGGT-3') (SEQ ID NO:3, where Y=C or T, M=A or C). The 16S rRNA gene sequence of each isolate was used as the query sequence for a BLAST search (Altschul et al., Nucleic Acids Res., 25:3389–3402(1997)) of GenBank® for similar sequences.

A 16S rRNA gene of strain AN12 was sequenced (SEQ ID NO:4) and compared to other 16S rRNA sequences in the GenBank® sequence database. The 16S rRNA gene sequence from strain AN12 was 98% similar to the 16S rRNA gene sequences of high G+C Gram positive bacteria *Rhodococcus erythropolis*.

with 10 μg/mL tetracycline. The pBR328 vector does not replicate in *Rhodococcus* and the tetracycline resistant transformants obtained after 3–4 days of incubation at 30° C. were generated by chromosomal integration. Integration into the targeted crtO gene on chromosome of 47072 was confirmed by PCR. The vector specific primers PBR3 (5'-AGCGGCATCAGCACCTTG-3'; SEQ ID NO:9) and PBR5 (5'-GCCAATATGGACAACTTCTTC-3'; SEQ ID NO:10), paired with the gene specific primers (outside of the insert on pDCQ102) I2_OP5 (5'-ACCTGAGGTGTTCGACGAG-GACMCCGA-3'; SEQ ID NO:11) and I2_OP3 (5'-GTTG-CACAGTGGTCATCGTGCCAGCCGT-3'; SEQ ID NO:12) were used for PCR with chromosomal DNA prepared from the tetracycline resistant transformants as template. PCR fragments of the expected size were amplified from the tetracycline resistant transformants, but no PCR product was obtained from the wild-type 47072. When the two gene specific primers were used, no PCR fragment was obtained with the tetracycline resistant transformants due to the insertion of the large vector DNA. The PCR fragment obtained with the vector specific primers and the gene specific primers was sequenced. Sequence analysis of the junction of the vector and the crtO gene confirmed that the single crossover recombination occurred at the expected site and disrupted the targeted CrtO gene.

TABLE 1

| Gene Name and Organism of Isolation | Similarity Identified | SEQ ID | % Identity[a] | % Similarity[b] | E-value[c] | Citation |
|---|---|---|---|---|---|---|
| crtO *Rhodococcus erythropolis* AN12 | phytoene dehydrogenase, putative [*Deinococcus radiodurans*] (AE001872) | 7 | 35 | 50 | 6e–75 | White, O. et al., Genome sequence of the radioresistant bacterium *Deinococcus radiodurans* R1 Science. 286 (5444), 1571–1577 (1999) |
| crtO *Rhodococcus erythropolis* ATCC47072 | phytoene dehydrogenase, putative [*Deinococcus radiodurans*] (AE001872) | 8 | 36 | 51 | 1e–72 | White, O. et al., Genome sequence of the radioresistant bacterium *Deinococcus radiodurans* R1 Science. 286 (5444), 1571–1577 (1999) |

Example 2

Construction of the *Rhodococcus* crtO Knockout Mutant as the Production Host

The crtO knockout mutant of *Rhodococcus erythropolis* ATCC 47072, hereafter referred to as 47072, was generated by homologous recombination using the following procedure. PCR primers AN12_I2_F (5'-CCATGGTCTGCGCACCTCATGATCCGA-3': SEQ ID NO:5) and AN12_I2_R (5'-CCATGGAATGAAGCGGTCGAGGACGGA-3': SEQ ID NO:6) were designed based on the *Rhodococcus erythropolis* AN12 crtO sequence (SEQ ID NO:7), the underlined sequences were the engineered NcoI sites. The primers were used to amplify the 1151 bp crtO internal fragment from 47072 with a 275 bp truncation at the N-terminal end and 173 bp truncation at the C-terminal end of the gene. The crtO amplified from 47072 (SEQ ID NO:8) was confirmed by sequencing and showed 95% identity at the DNA level with the AN12 crtO The crtO fragment was first cloned into pCR2.1 TOPO vector (Invitrogen, Carlsbad, Calif.). The TOPO clones were then digested with NcoI and the crtO fragment was subsequently cloned into the NcoI site of pBR328 (GenBank® Accession #L08858). The resulting construct was confirmed by sequencing and designated as pDCQ102. Approximately 1 μg DNA of PDCQ102 was introduced into 47072 by electroporation and plated on NBYE (0.8% nutrient broth and 0.5% yeast extract) plates The sequence of crtO was compared for similarity with other sequences by conducting BLAST (Basic Local Alignment Search Tool; Altschul, S. F., et al., *J. Mol. Biol.*, 215:403–410 (1993)) searches against the "nr" database (comprising all non-redundant GenBanke® CDS translations, sequences derived from the 3-dimensional structure Brookhaven Protein Data Bank, the SWISS-PROT protein sequence database, EMBL, and DDBJ databases). These sequences were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX BLOSUM62 algorithm with a gap existence cost of 11 per residue gap cost of 2, filtered, gap alignment (Gish, W. and States, D. J., *Nature Genetics*, 3:266–272 (1993)) provided by the NCBI.

The results of the BLAST comparisons are given in Table 1, which summarize the sequence to which each sequence has the most similarity. Table 1 displays data based on the BLASTXnr algorithm with values reported in expect values. The Expect value estimates the statistical significance of the match, specifying the number of matches, with a given score, that are expected in a search of a database of this size absolutely by chance.

Although the BLAST analysis indicated that CrtO had the highest homology to phytoene dehydrogenases, knockout mutants of CrtO suggested that CrtO encodes a carotenoid ketalase. Colonies of the crtO mutant, 47072 (crtO-), were yellow compared to the pink color of the 47072 wild-type strain, which suggested that different carotenoid pigments were produced in the crtO mutant, 47072 (crtO-). To extract the carotenoids from 47072 (crtO-), 100 mL of cell culture in NBYE (0.8% nutrient broth +0.5% yeast extract) was grown at 26° C. to the stationary phase in aerobic conditions. Cells were spun down at 4000 g for 15 min, and the cell pellets were resuspended in 10 mL acetone. Carotenoids were extracted into acetone with constant shaking at room temperature for 1 hour. The cells were spun down and the supernatant was collected. The extraction was repeated once, and the supernatants of both extractions were combined and dried under nitrogen. The dried material was re-dissolved in 0.5 mL methanol and insoluble material was removed by centrifugation at 16,000 g for 2 min. The sample was analyzed by HPLC using a Beckman System Gold® HPLC with Beckman Gold Nouveau Software (Columbia, Md.). The extract (0.1 mL) was loaded onto a 125×4 mm RP8 (5 μm particles) column with corresponding guard column (Hewlett-Packard, San Fernando, Calif.). The flow rate was 1 mL/min. The solvent program was: 0–11.5 min linear gradient from 40% water/60% methanol to 100% methanol, 11.5–20 min 100% methanol, 20–30 min 40% water/60% methanol. The spectra data were collected by a Beckman photodiode array detector (model 168). HPLC analysis showed that 47072 (crtO-) lacked the major carotenoid peak of the wild-type strain. The major peak observed in 47072 (crtO-) was at an elution time of 15.5 and the absorption maxima were 435 nm, 458 nm and 486 nm, which is identical to the characteristics of γ-carotene. Thus, ATCC 47072 (crtO-) accumulated γ-carotene and could be used as an expression host for crtU to synthesize aromatic carotenoids.

Example 3

Construction of pRhBR171 and pDCQ23 Shuttle Vectors

An *E. coli-Rhodococcus* shuttle vector requires a set of replication function and antibiotic resistance markers that functions both in *E. coli* and in *Rhodococcus*. Applicants have identified a cryptic pAN12 plasmid which encodes the replication function for *Rhodococcus*. To identify an antibiotic resistance marker for *Rhodococcus*, *E. coli* plasmid pBR328 (ATCC #37517, GenBank® Accession #L08858) was tested to see whether it would function in *Rhodococcus*. Plasmid pBR328 carries ampicillin, chloramphenicol, and tetracycline resistance markers that function in *E. coli*. pBR328 was linearized with PvuII which disrupted the chloramphenicol resistance gene and ligated with pAN12 digested with SspI. The resulting clone was designated pRhBR17 (SEQ ID NO:13).

Transposon mutagenesis of the shuttle plasmid pRhBR17 suggested that certain regions of the shuttle plasmid may not be essential for the plasmid function (Table 2). One of these regions was at the junction of pBR328 and pAN12. It was decided to examine whether this region of the plasmid was dispensable and if the size of the shuttle plasmid could be trimmed. Shuttle plasmid pRhBR17 was digested with Pst I (2 sites/2520, 3700 bp) and Mlu I (1 site/4105 bp), yielding three fragments of the following sizes: 9656, 1180 and 405 bp. The digested DNA fragments were blunt ended with mung bean nuclease (New England Biolabs, Beverly, Mass.) following manufacturer's instruction. The largest 9.7 kb fragment was separated by size on an agarose gel, and purified using QIAEX II Gel Extraction Kit (Qiagen). This 9.7 kb DNA fragment with deletion of region 2520–4105 bp of pRhBR17 was self-ligated to form a circular plasmid designated pRhBR171. Plasmid isolation from the *E. coli* DH10B transformants and restriction enzyme characterization showed the correct size and digest pattern of pRhBR171. *E. coli* cells harboring the pRhBR171 plasmid lost the ability to grow in the presence of ampicillin (100 μg/mL), since the Pst I and Mlu I digest removed part of the coding region for the ampicillin resistant gene on the parental plasmid. The tetracycline resistance gene on pRhBR171 served as the selection marker for both *E. coli* and *Rhodococcus*. Transformation of pRhBR171 to *Rhodococcus* was tested. It transformed competent *Rhodococcus erythropolis* ATCC 47072 and AN12 cells with similar frequency by electroporation as compared with its parental plasmid pRhBR17. These results demonstrate that this region (2520–4105 bp) of pRhBR17 was not essential as suggested by transposon mutagenesis. It also provided a smaller shuttle vector that is more convenient for cloning.

TABLE 2

Transposon insertion mapping of pRhBR17 and the effects on transformation of *Rhodococcus* ATCC 47072

| Clone number | Site inserted | Strand inserted | Gene inserted | Transformation ability |
|---|---|---|---|---|
| pRhBR17 | No insertion | N/A | N/A | +++ |
| 30, 31 | 2092 bp | Forward | pBR328 | +++ |
| 26, 27 | 3120 bp | Reverse | pBR328 | ND |
| 29 | 3468 bp | Reverse | pBR328 | ND |
| 24 | 3625 bp | Reverse | pAN12 | +++ |
| 2 | 4030 bp | Reverse | pAN12 | +++ |
| 38, 39 | 4114 bp | Forward | pAN12 | +++ |
| 20 | 4442 bp | Reverse | pAN12 | +++ |
| 1 | 4545 bp | Reverse | pAN12 | +++ |
| 35 | 4568 bp | Forward | pAN12 | +++ |
| 13 | 4586 bp | Forward | pAN12 | + |
| 17, 33 | <4920 bp | Forward | pAN12 | + |
| 7 | 5546 bp | Forward | pAN12 rep | + |
| 11 | 5739 bp | Reverse | pAN12 rep | – |
| 12 | 5773 bp | Forward | pAN12 rep | – |
| 16 | 5831 bp | Forward | pAN12 rep | – |
| 5 | 5883 bp | Reverse | pAN12 rep | – |
| 9 | 6050 bp | Reverse | pAN12 rep | – |
| 28 | 6283 bp | Forward | pAN12 rep | – |
| 6 | 6743 bp | Reverse | pAN12 | – |
| 37 | <6935 bp | Forward | pAN12 | +++ |
| 32 | 6965 bp | Forward | pAN12 | +++ |
| 15 | 6979 bp | Forward | pAN12 | + |
| 3 | 7285 bp | Reverse | pAN12 | +++ |
| 4 | 7811 bp | Reverse | pAN12 | +++ |
| 22, 23 | 8274 bp | Forward | pAN12 div | +++ |
| 21 | 8355 bp | Forward | pAN12 div | +++ |
| 18 | 8619 bp | Reverse | pAN12 div | +++ |
| 10 | 10322 bp | Reverse | pBR328 | +++ |
| 36 | 11030 bp | Forward | pBR328 | ND |

+++ the transformation frequency was comparable to that of the wild type plasmid.
+ the transformation frequency decreased about 100 fold.
– the transformation frequency was zero.
ND the transformation frequency was not determined.

The dxs gene (SEQ ID NO:14) with its native promoter was amplified from the *Rhodococcus* AN12 strain by PCR. Two upstream primers, New dxs 5' primer, 5'-ATT TCG TTG AAC GGC TCG CC-3' (SEQ ID NO:15), and New2 dxs 5' primer, 5'-CGG CM TCC GAC CTC TAC CA-3' (SEQ ID NO:16), were designed to include the native promoter region of dxs with different lengths. The downstream primer, New dxs 3' primer, 5'-TGA GAC GAG CCG <u>TCA</u> GCC TT-3' (SEQ ID NO:17), included the underlined stop codon of the dxs gene. PCR amplification of AN12 total DNA using New dxs 5'+ New dxs 3' yielded one product of 2519 bp in size, which included the full length AN12 dxs coding region and about 500 bp of immediate upstream region (nt. #500-#3019). When using New2 dxs 5'+ New dxs 3' primer pair, the PCR product is 2985 bp in size, including the complete AN12 dxs gene and about 1 kb upstream region (nt. #34-#3019). Both PCR products were cloned in the pCR2.1-TOPO cloning vector according to manufacturer's instruction (Invitrogen). Resulting clones were screened and sequenced. The confirmed plasmids were digested with EcoRI and the 2.5 kb and 3.0 kb fragments containing the dxs gene and the upstream region from each plasmid were treated with the Klenow enzyme and cloned into the unique Ssp I site of the *E. coli* —*Rhodococcus* shuttle plasmid pRhBR171. The resulting constructs pDCQ22 (clones #4 and #7) and pDCQ23 (clones #10 and #11) were electroporated into *Rhodococcus erythropolis* ATCC 47072 with tetracycline 10 µg/mL selection.

The pigment of the *Rhodococcus* transformants of pDCQ22 and pDCQ23 appeared darker as compared with those transformed with the vector control. To quantify the carotenoid production of each *Rhodococcus* strain, 1 mL of fresh cultured cells were added to 200 mL fresh LB medium with 0.05% Tween-80 and 10 µg/mL tetracycline, and grown at 30° C. for 3 days to stationary phase (Table 3). Cells were pelleted by centrifugation at 4000 g for 15 min and the wet weight was measured for each cell pellet. Carotenoids were extracted from the cell pellet into 10 mL acetone overnight with shaking and quantitated at the absorbance maximum (465 nm). The 465 nm wavelength was diagnostic of the absorbance peak for the carotenoid isolated from *Rhodococcus* sp. ATCC 47072. The absorption data was used to calculate the amount of carotenoid produced. This amount was calculated and normalized in each strain based either on the cell paste weight or the cell density (OD600). Carotenoid production calculated by either method showed about 1.6-fold increase in 47072 with pDCQ22, which contained the dxs gene with the shorter promoter region.

Example 4

Expression of *Brevibacterium* crtU Downstream of dxs Gene in *Rhodococcus*

The dxs gene (SEQ ID NO:14) encodes the 1-deoxyxylulose-5-phosphate synthase that catalyzes the first step of the synthesis of 1-deoxyxylulose-5-phosphate from glyceraldehyde-3-phosphate and pyruvate precursors in the isoprenoid pathway for carotenoid synthesis. As indicated in Example 3, placement of the *Rhodococcus* dxs gene with its native promoter on a multicopy shuttle vector (pDCQ23) increased *Rhodococcus* carotenoid production approximately 2-fold. Initially, the *Brevibacterium* crtU gene (SEQ ID NO: 18) (Krubasik et al., *Mol. Gen. Genet.*, 263:423–432 (2000)) was cloned downstream of the dxs gene on pDCQ23. The rational behind this strategy was two-fold. First, the crtU gene could be expressed in *Rhodococcus* by the dxs promoter, which had been demonstrated to be functional on pDCQ23. Second, the *Rhodococcus* strain with pDCQ23 produced twice as much carotenoid as compared with 47072 not carrying dxs (Table 3). A unique MscI site on pDCQ23 was identified immediately downstream of dxs into which the crtU gene was cloned to form a polycistronic transcript. The crtU gene with its native ribosome binding site was amplified from genomic DNA of *Brevibacterium linens* (ATCC 9175) by PCR, using forward primer crtU_RBS(Brevi) (5'-GTGCTCATGCTGTGGCAGTG-GCM-3' SEQ ID NO:20) and reverse primer crtU_R (5'-TCATCGACGTCTCCTGATGAGCCCGAGCACT-3' SEQ ID NO:21). The 1554 bp PCR product was first cloned in the pCR2.1-TOPO cloning vector (Invitrogen), resulting in plasmid pDCQ138. The 1.6 kb EcoRI fragment of pDCQ138 DNA containing the crtU gene was filled in by Klenow DNA polymerase and ligated to the MscI site in pDCQ23. In the resulting construct PDCQ139, the crtU gene was in the same orientation as the dxs gene. No transcription

TABLE 3

Carotenoids production by *Rhodococcus* strains.

| Strain | OD600 | weight (g) | OD465 | %[a] | % (wt)[b] | % (OD600)[c] | % (avg)[d] |
|---|---|---|---|---|---|---|---|
| 47072 (pRhBR171) | 1.992 | 2.82 | 0.41 | 100 | 100 | 100 | 100 |
| 47072 (pDCQ22)#4 | 1.93 | 2.9 | 0.642 | 157 | 161 | 152 | 156 |
| 47072 (pDCQ22)#7 | 1.922 | 2.76 | 0.664 | 162 | 159 | 156 | 157 |
| 47072 (pDCQ23)#10 | 1.99 | 2.58 | 0.958 | 234 | 214 | 233 | 224 |
| 47072 (pDCQ23)#11 | 1.994 | 2.56 | 0.979 | 239 | 217 | 239 | 228 |

[a]% of carotenoid production based on OD465 nm.
[b]% of carotenoid production (OD465 nm) normalized with wet cell paste weight.
[c]% of carotenoid production (OD465 nm) normalized with cell density (OD600 nm).
[d]% of carotenoid production (OD465 nm) averaged from the normalizations with wet cell paste weight and cell density.

Figure 3:
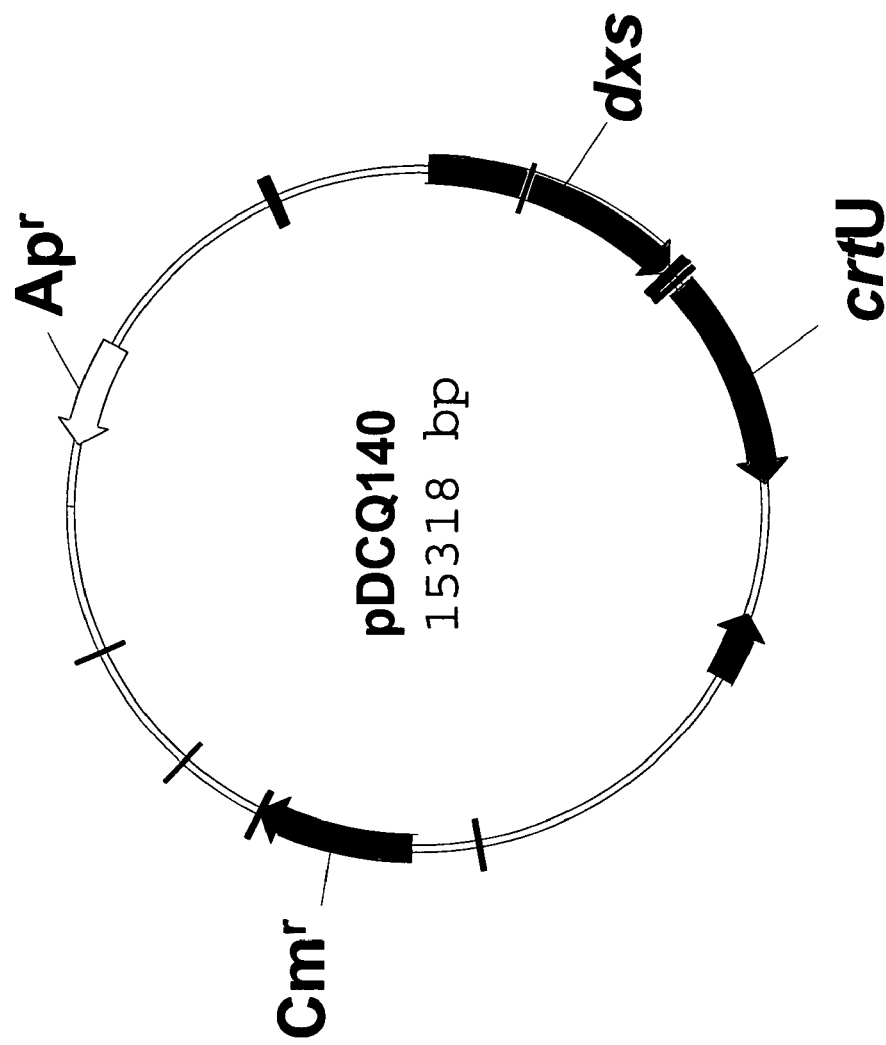
FIG. 3 is a plasmid map of pDCQ140 with crtU expression downstream of dxs gene on a pDA71 based *Rhodococcus* shuttle vector.
Figure 4:
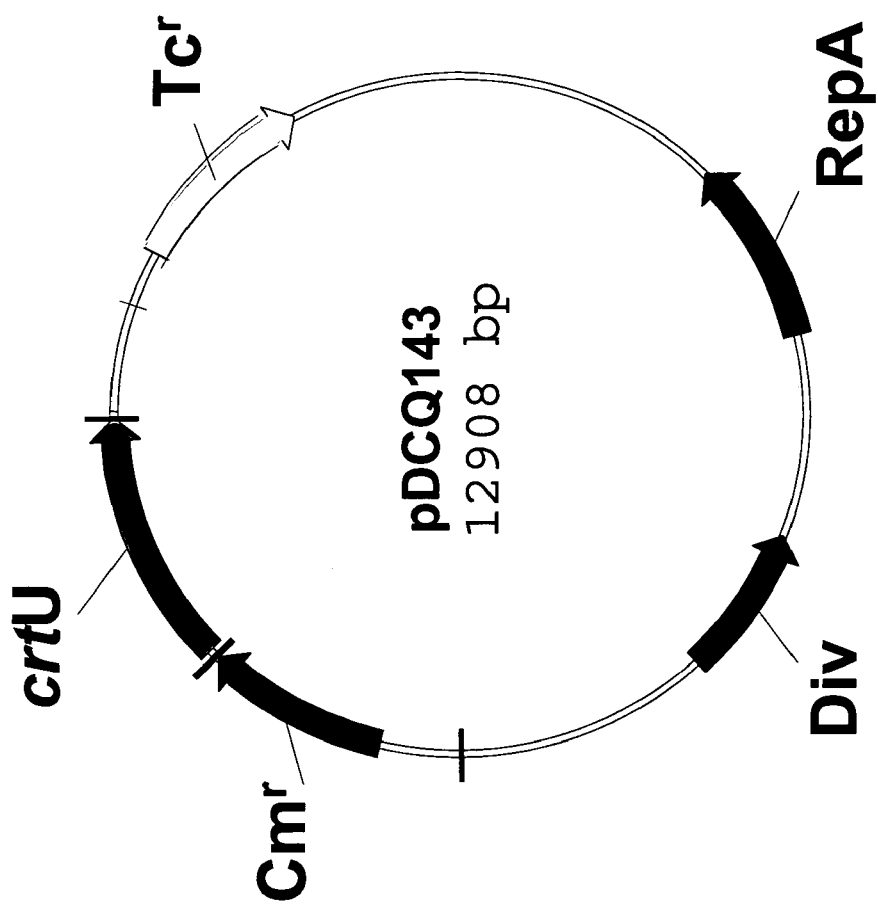
FIG. 4 is a plasmid map of pDCQ143 with crtU expression downstream of $Cm^r$ gene on a pRhBR171 based *Rhodococcus* shuttle vector.

Carotenoid production increased even more (2.2-fold) when the dxs gene was expressed with the longer promoter region as in pDCQ23 (Table 3). It is likely that the 1 kb upstream DNA contains the promoter and some elements for enhancement of the expression. HPLC analysis also verified that the same carotenoids were produced by the wild-type strain, 47072 (pRhBR171), and the dxs expression strain, 47072 (pDCQ22) or (pDCQ23).

termination site was found between dxs and crtU, which are separated by 131 bp of DNA sequence. The crtU presumably was co-transcribed with the dxs gene. The pDCQ139 construct contained a tetracycline resistant marker, which was the same marker as the one used to create the crtO knockout host as described in Example 2. The 6.0 kb Hind III fragment containing the dxs and crtU gene cluster was cut out from pDCQ 139 and ligated to the HindIII site of another *Rhodococcus* shuttle vector pDA71 (ATCC 77474) (FIG. 4), which has a chloramphenicol resistant marker (GenBank® Accession #AJ308376, SEQ ID NO:22) for selection in *Rhodococcus*. The resulting construct, pDCQ140, (FIG. 3) was verified by sequencing. Plasmid pDCQ140 and the vector control pDA71 were electroporated into 47042 (crtO-). Cells were grown in 200 mL LB with 0.05% Tween-80, 10 µg/mL tetracycline and 40 µg/mL chloramphenicol at 30° C. for 2 days. Carotenoids were extracted from cell pellets with 20 mL acetone, dried under nitrogen and dissolved in 1 mL methanol. Each sample of 0.1 mL was used for HPLC analysis as described in Example 2. In 47042 (crtO-), carrying the pDA71 vector control (FIG. 4), the γ-carotene eluted at 15.4 min. In the 47042 (crtO-), with pDCQ140 containing crtU, the majority of the carotenoids was γ-carotene, which eluted at 15.4 min. However, a new carotenoid representing 7% of the total carotenoids eluted at 15.1 min. This new carotenoid was the conversion product of CrtU, chlorobactene, and was confirmed as is described in subsequent examples.

Example 5

Expression of *Brevibacterium* crtU Downstream of $Cm^r$ Gene in *Rhodococcus*

Only a small fraction of γ-carotene was converted by crtU downstream of dxs on pDCQ140. Since dxs was shown to be a limiting step for carotenoid synthesis in *E. coli* (Albrecht, M., et al., *Biotechnol. Letters*, 21:791–795 (1999)), it is likely that the promoter of dxs was also not strong in *Rhodococcus*. One way to improve the crtU expression was to use a stronger promoter. The promoter of the $Cm^r$ gene on pDA71 (SEQ ID NO:22) was a likely candidate. Another advantage of using the promoter of the $Cm^r$ gene was that this $Cm^r$ gene only expresses in *Rhodococcus* and not in *E. coli*, which circumvented toxicity or stability problems in *E. coli* during sub-cloning steps. The $Cm^r$ gene on pDA71 has been used as an antibiotic marker cassette and the gene and its promoter was previously localized to the 1.8 kb BbrPI-StuI fragment (De Mot, R., et al., *Microbiology*, 143:3137–3147 (1997); GenBank® Accession #AJ308376). The $Cm^r$ gene including 500 bp of its upstream region was PCR amplified from pDA71 plasmid DNA, using forward primer cm_F (5'-ccatggcgaagtaccgtcacgtgcac-3'; SEQ ID NO:23) and reverse primer cm_R (5'-ccatggcaattgtcaggctgggacggtttcct-3'; SEQ ID NO:24). The forward primer, cm_F, spanned the BbrPI site (bold). The reverse primer, cm_R, contained the complementary sequence of a stop codon of the gene shown in bold. Both primers contained NcoI sites (underlined) and cm_R contained a MfeI site (italicized). The 1640 bp PCR product was cloned in the pCR2.1-TOPO cloning vector (Invitrogen), resulting in pDCQ141. The 1.6 kb NcoI fragment from pDCQ141 was subcloned into the NcoI site in pRhBR171 to construct the new *E. coli—Rhodococcus* shuttle plasmid pDCQ142 with the $CM^r$ gene. The 1.6 kb EcoRI fragment of PDCQ138 DNA containing the crtU gene and its ribosomal binding site was subcloned into the unique MfeI site immediately downstream of $Cm^r$ gene in pDCQ142. The resulting construct pDCQ143 contained the crtU gene downstream of the $Cm^r$ gene, with both $Cm^r$ and crtU oriented in the same direction. The two genes were separated by 62 bp DNA without an apparent transcriptional termination site. The crtU gene could presumably be transcribed as a polycistronic message with the $Cm^r$ gene by its promoter. Plasmid pDCQ143 and the vector control pDCQ142 were electroporated into 47042 (crtO-). Cells were grown in 200 mL LB with 0.05% Tween-80, 10 µg/mL tetracycline and 40 µg/mL chloramphenicol at 30° C. for 2 days. Carotenoids were extracted from cell pellets with 20 mL acetone, dried under nitrogen and dissolved in 1 mL methanol. Each sample of 0.1 mL was used for HPLC analysis as described in Example 2. In 47042 (crtO-), with the pDCQ142 vector control, γ-carotene eluted at 15.3 min. In 47042 (crtO-), with pDCQ143 containing crtU, no carotenoid eluted at 15.3 and all carotenoid eluted at 15.0 min. Since the carotenoid that eluted at 15.0 min has the same absorption spectra as γ-carotene (which eluted at 15.3 min), it was not certain that the carotenoid at 15.0 min is a new carotenoid produced by pDCQ143 or whether the γ-carotene eluted at slightly different position due to HPLC variation. To distinguish these two possibilities, equal amounts of carotenoids extracted from the pDCQ142 control strain and the strain with pDCQ143 were mixed and loaded on HPLC. Two carotenoids peaks were observed with 41% eluting at 15.0 min and 59% eluting at 15.3 min. This strongly suggested that the carotenoid produced from the strain containing pDCQ143 was different from the γ-carotene produced from the pDCQ142 vector control strain. The crtU expressed downstream of $CM^r$ gene on pDCQ143 achieved nearly 100% conversion of γ-carotene to the new carotenoid, which was analyzed as described in Example 6.

Example 6

Confirmation of Synthesis of Chlorobactene in *Rhodococcus* by LC-MS

Chlorobactene exhibits the same absorption spectra as γ-carotene. In order to confirm synthesis of chlorobactene in *Rhodococcus*, molecular weight of the carotenoids from different *Rhodococcus* strains were determined by LC-MS. Carotenoids were extracted as described above from wild type *Rhodococcus erythropolis* ATCC 47072, 47072 (crtO-), and 47072 (crtO-) containing pDCQ143. Each sample of 50 µL was run on a Zorbax 2.1×150 mm SB-C18 LC column isocraticly with 75% acetonitrile and 25% acetone for 30 minutes (Agilent Technologies, Calif.). The mass spectrometer (a Micromass Quattro LC triple quadrapole, Micromass Limited, UK) was scanned from 100 to 1000 AMU's in 0.9 seconds with an 0.1 second interscan delay in APCI (Atomopheric Pressure Chemical Ionization) mode with the corona discharge needle at 3 KV and the APCI probe at 450 degrees centigrade. Results of LC-MS analyses are shown in FIG. 5. As expected, wild type ATCC 47072 produced 4-keto-γ-carotene with a molecular weight of 550 Dalton (FIG. 5), 47072 (crtO-) produced γ-carotene with molecular weight of 536 Dalton, and 47072 (crtO-) containing pDCQ143 produced a new carotenoid with molecular weight of 532 Dalton. The 4 Dalton difference of molecular weight between γ-carotene and the new carotenoid was consistent with the aromatization of the β-ionone ring of the γ-carotene by two additional steps of desaturation. The new carotenoid produced in 47072 (crtO-) containing pDCQ143 was chlorobactene, the aromatized product from γ-carotene catalyzed by CrtU.

Example 7

Production of Chlorobactene in the Wild Type *Rhodococcus erythropolis*

As mentioned in the Example 2, the carotenoid ketolase CrtO (SEQ ID NO:8) found in the wild type *Rhodococcus erythropolis* ATCC 47072 would compete with the heterologous aromatase CrtU for the γ-carotene substrate. The crtU gene was therefore expressed in the 47072 (crtO-) as described above. The question of whether significant amount of chlorobactene could be produced from the wild type ATCC 47072 host was also addressed. The wild type strain has no antibiotic selection for the host and higher growth rate. Plasmid pDCQ143 containing the *Brevibacterium* crtU expressed downstream of the Cm$^r$ gene was transformed into the wild type *Rhodococcus* ATCC 47072 strain and transformants were selected on LB with 40 μg/mL chloramphenicol plates. Carotenoids were extracted from the transformants and analyzed as described in Example 2. HPLC analysis indicated that majority of the carotenoids produced was chlorobactene. Less than 10% of carotenoids present was 4-keto-γ-carotene, which eluted at 14.5 min (absorption maximum at 465 nm). Samples were also concentrated and spotted on a 250 μm thickness Silica Gel 60 plate (EM Separations Technology, Gibbstown, N.J.) for thin layer chromatography (TLC). FIG. 6 illustrated comparison of carotenoids from wild type *Rhodococcus* 47072, 47072 (crtO-), 47072 with pDCQ143, and 47072 (crtO-) with pDCQ143 separated on the Silica TLC in 7.5% acetone +92.5% hexane. 4-keto-γ-carotene in the wild type, γ-carotene in 47072 (crtO-), and chlorobactene in crtO⁻ (pDCQ143) was previously confirmed by LC/MS as shown in FIG. 5. In the 47072 carrying pDCQ143, a mixture of chlorobactene and 4-keto-γ-carotene was produced as expected. The fact that majority of carotenoids in the mixture was chlorobactene indicated that it was feasible to use the wild type ATCC 47072 as the crtU expression host for the production of chlorobactene. The crtU expressed from the pDCQ143 plasmid competed well with the single copy crtO encoded on the chromosome of ATCC 47072.

What is claimed is:

1. A method for the production of chlorobactene comprising:
   (a) providing a Rhodococcus host cell which comprises γ-carotene;
   (b) transforming the host cell of (a) with a gene encoding a polypeptide having the amino acid sequence as set forth in SEQ ID NO:19; and
   (c) growing the transformed host cell of (b) under conditions whereby an aryl carotenoid is produced.

2. A method according to claim 1 wherein the gene encoding a polypeptide having an amino acid sequence as set forth in SEQ ID NO: 19 under the control of a promoter derived from a chloramphenicol resistance agent.

3. A method according to claim 1 wherein the host cell is *Rhodococcus erythropolis*.

4. A method according to claim 1 wherein the γ-carotene is produced endogenously by the host cell.

* * * * *

UNITED STATES PATENT AND TRADEMARK OFFICE
CERTIFICATE OF CORRECTION

| | | |
|---|---|---|
| PATENT NO. | : 7,186,523 B2 | Page 1 of 1 |
| APPLICATION NO. | : 10/430129 | |
| DATED | : March 6, 2007 | |
| INVENTOR(S) | : Qiong Cheng, Pierre E. Rouviere and Luan Tao | |

It is certified that error appears in the above-identified patent and that said Letters Patent is hereby corrected as shown below:

TITLE PAGE
Item (75) Inventors: "Pierre E. Rouvier" should read --Pierre E. Rouviere--

Signed and Sealed this

Twenty-second Day of May, 2007

JON W. DUDAS
*Director of the United States Patent and Trademark Office*